United States Patent
Bhatia et al.

(10) Patent No.: US 9,611,453 B2
(45) Date of Patent: Apr. 4, 2017

(54) MICROMECHANICAL DEVICES FOR CONTROL OF CELL-CELL INTERACTION, AND METHODS OF USE THEREOF

(75) Inventors: Sangeeta N. Bhatia, Lexington, MA (US); Elliot Hui, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 1152 days.

(21) Appl. No.: 12/449,994

(22) PCT Filed: Mar. 10, 2008

(86) PCT No.: PCT/US2008/056403
§ 371 (c)(1),
(2), (4) Date: Mar. 15, 2010

(87) PCT Pub. No.: WO2008/109883
PCT Pub. Date: Sep. 12, 2008

(65) Prior Publication Data
US 2010/0167330 A1 Jul. 1, 2010

Related U.S. Application Data

(60) Provisional application No. 60/893,736, filed on Mar. 8, 2007.

(51) Int. Cl.
*C12Q 1/02* (2006.01)
*C12M 1/42* (2006.01)
*C12M 1/12* (2006.01)
*C12M 1/00* (2006.01)

(52) U.S. Cl.
CPC .......... *C12M 35/08* (2013.01); *C12M 23/04* (2013.01); *C12M 23/20* (2013.01)

(58) Field of Classification Search
None
See application file for complete search history.

(56) References Cited

U.S. PATENT DOCUMENTS

| 7,968,331 B2 * | 6/2011 | Cheong et al. ............ 435/299.1 |
| 2004/0214313 A1 | 10/2004 | Zhang et al. |
| 2007/0249041 A1 | 10/2007 | Cheong et al. |

FOREIGN PATENT DOCUMENTS

| EP | 1847592 A1 | 10/2007 |
| WO | WO 00/65137 * | 11/2000 |
| WO | 02/092778 A2 | 11/2002 |
| WO | WO2005060396 * | 7/2005 |
| WO | WO 2006015368 * | 2/2006 ............ C07K 14/47 |
| WO | 2006/116752 A2 | 11/2006 |
| WO | 2008/109883 A3 | 9/2008 |

OTHER PUBLICATIONS

Gaillard et al., "Establishment and functional characterization of an in vitro model of the blood-brain barrier, comprising a co-culture of brain capillary endothelial cells and astrocytes", European Journal of Pharmaceutical Sciences, 2001, vol. 12, pp. 215-222.*
Bhatia, Sangeeta N. et al., "Controlling cell interactions by micropatterning in co-cultures: Hepatocytes and 3T3 fibroblasts," Journal of Biomedical Materials Research, vol. 34:189-199 (1997).
Bhatia, S.N. et al., "Effect of cell-cell interactions in preservation of cellular phenotypes: cocultivation of hepatocytes and nonparenchymal cells," FASEB J., vol. 13:1883-1900 (1999).
Hui, Elliot E. et al., "Micromechanical control of cell-cell interacations," PNAS, vol. 104(14):5722-5726 (2007).
Hui, Elliot E et al., "Microscale Control of Cell Contact and Spacing via three-component surface patterning," Langmuir, vol. 23(8):4103-4107 (2007).
Hui, Elliot E. et al., "Silicon Microchips for Manipulating Cell-cell Interaction," www.jove.com, 2 pages, (2007).
Australian Office Action for Application No. 2008222634, 4 pages, dated Sep. 6, 2012.
International Search Report for Application No. PCT/US2008/056403, 2 pages, dated Jan. 30, 2009.
Khademhosseini, A. et al., "Cell docking inside microwells within reversibly sealed microfluidic channels for fabricating multiphenotype cell arrays," Lab Chip, vol. 5, 1380-1386 (2005).

* cited by examiner

*Primary Examiner* — Laura Schuberg
(74) *Attorney, Agent, or Firm* — Nelson Mullins Riley & Scarborough LLP; Amy E. Mandragouras, Esq.; Ariana D. Harris

(57) ABSTRACT

The development and function of living tissues depends largely on interactions between cells that can vary in both time and space; however, temporal control of cell-cell interaction is experimentally challenging. By employing a micromachined silicon substrate with moving parts, herein is disclosed the dynamic regulation of cell-cell interactions via direct manipulation of adherent cells with micron-scale precision. The inventive devices and methods allow mechanical control of both tissue composition and spatial organization. The inventive device and methods enable the investigation of dynamic cell-cell interaction in a multitude of applications, such as intercellular communication, spanning embryogenesis, homeostasis, and pathogenic processes.

34 Claims, 18 Drawing Sheets

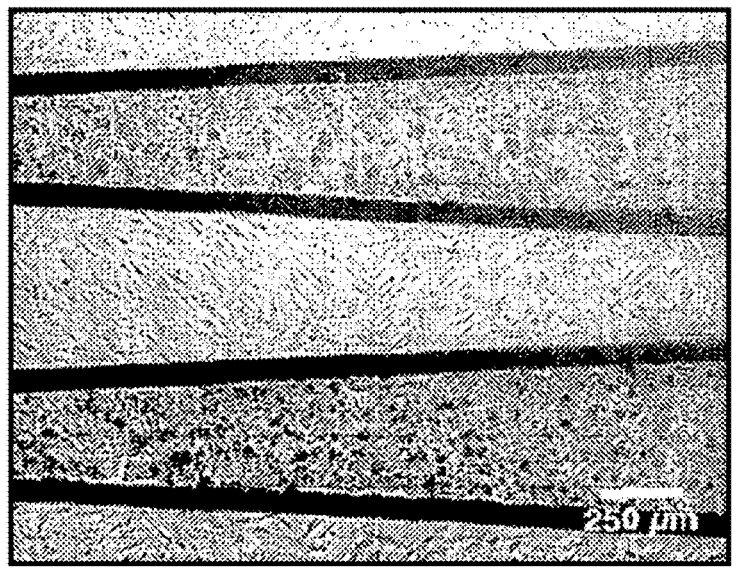
*Figure 1 cont.*

| Cytokine | Producing Cell | Target Cell | Function* |
|---|---|---|---|
| GM-CSF | Th cells | progenitor cells | growth and differentiation of monocytes and DC |
| IL-1α<br>IL-1β | monocytes<br>macrophages<br>B cells<br>DC | Th cells | co-stimulation |
| | | B cells | maturation and proliferation |
| | | NK cells | activation |
| | | various | inflammation, acute phase response, fever |
| IL-2 | Th 1 cells | activated T and B cells, NK cells | growth, proliferation, activation |
| IL-3 | Th cells<br>NK cells | stem cells | growth and differentiation |
| | | mast cells | growth and histamine release |
| IL-4 | Th2 cells | activated B cells | proliferation and differentiation IgG$_1$ and IgE synthesis |
| | | macrophages | MHC Class II |
| | | T cells | proliferation |
| IL-5 | Th2 cells | activated B cells | proliferation and differentiation IgA synthesis |
| IL-6 | monocytes<br>macrophages<br>Th2 cells<br>stromal cells | activated B cells | differentiation into plasma cells |
| | | plasma cells | antibody secretion |
| | | stem cells | differentiation |
| | | various | acute phase response |
| IL-7 | marrow stroma<br>thymus stroma | stem cells | differentiation into progenitor B and T cells |
| IL-8 | macrophages<br>endothelial | neutrophils | chemotaxis |
| IL-10 | Th2 cells | macrophages | *cytokine production* |
| | | B cells | activation |

*Figure 8A*

| Cytokine | Producing Cell | Target Cell | Function* |
|---|---|---|---|
| IL-12 | macrophages B cells | activated Tc cells | differentiation into CTL (with IL-2) |
| | | NK cells | activation |
| IFN-α | leukocytes | various | *viral replication* MHC I expression |
| IFN-β | fibroblasts | various | *viral replication* MHC I expression |
| IFN-γ | Th1 cells, Tc cells, NK cells | various | *Viral expression* |
| | | macrophages | MHC expression |
| | | activated B cells | Ig class switch to IgG$_{2a}$ |
| | | Th2 cells | *proliferation* |
| | | macrophages | pathogen elimination |
| MIP-1α | macrophages | monocytes, T cells | chemotaxis |
| MIP-1β | lymphocytes | monocytes, T cells | chemotaxis |
| TGF-β | T cells, monocytes | monocytes, macrophages | chemotaxis |
| | | activated macrophages | IL-1 synthesis |
| | | activated B cells | IgA synthesis |
| | | various | *proliferation* |
| TNF-α | macrophages, mast cells, NK cells | macrophages | CAM and cytokine expression |
| | | tumor cells | cell death |
| TNF-β | Th1 and Tc cells | phagocytes | phagocytosis, NO production |
| | | tumor cells | cell death |

*Figure 8B*

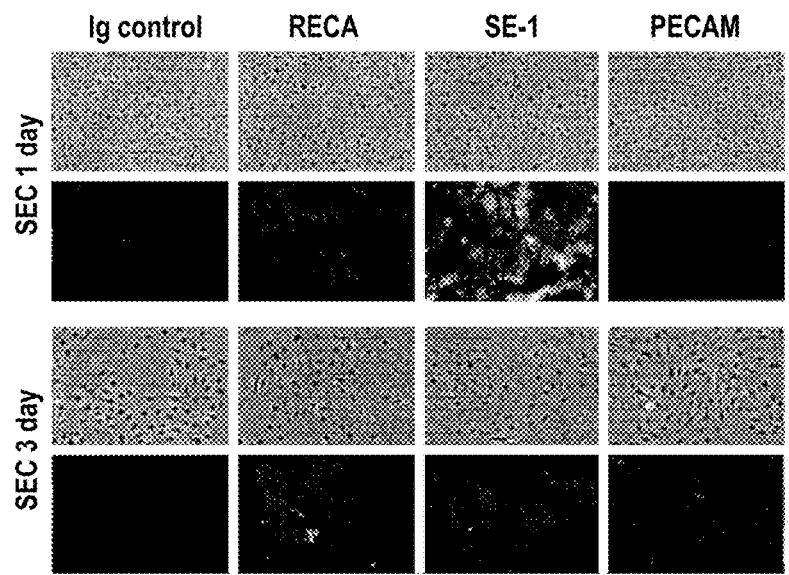
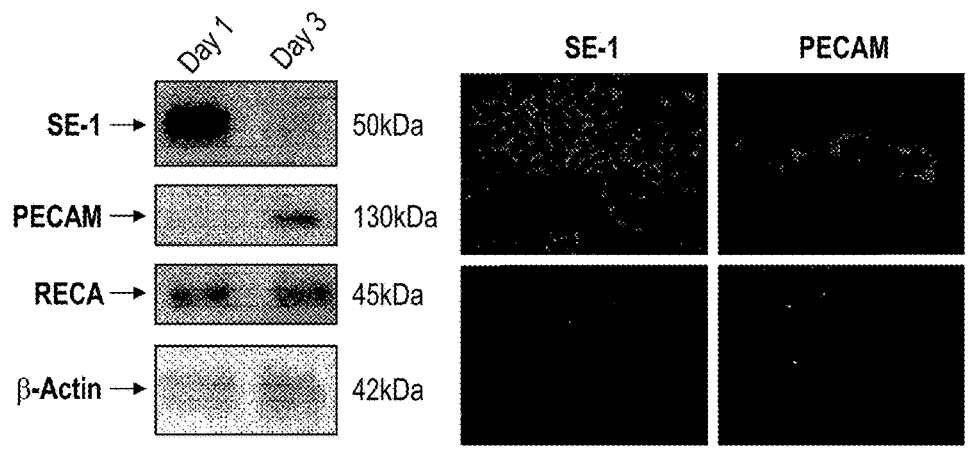
*Figure 9*

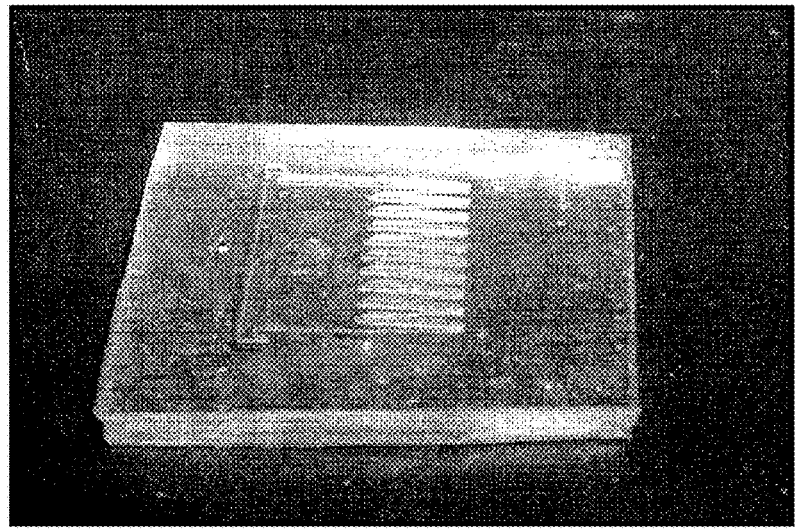
A
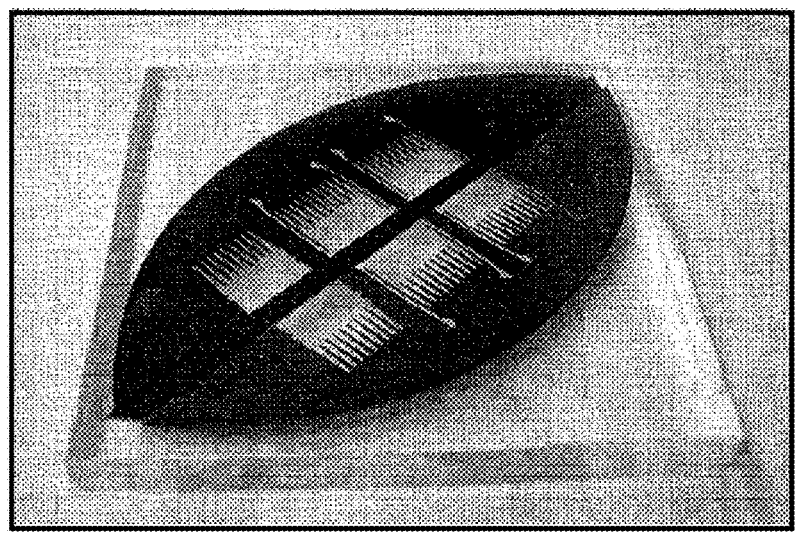
B
Figure 12

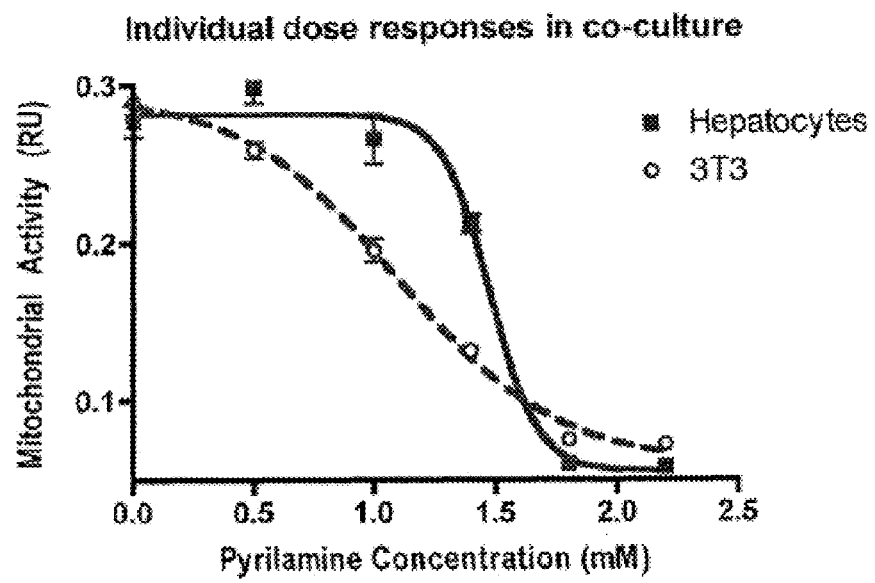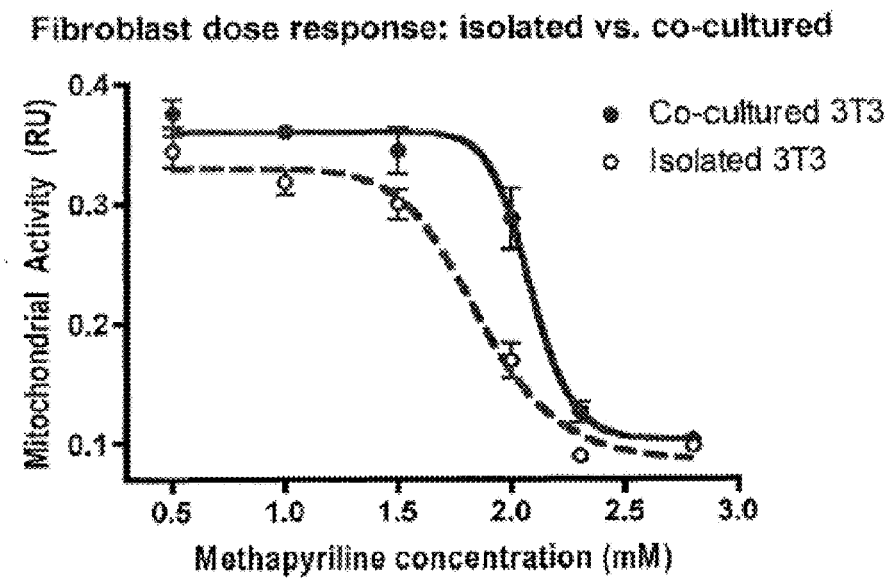
Figure 13

MICROMECHANICAL DEVICES FOR CONTROL OF CELL-CELL INTERACTION, AND METHODS OF USE THEREOF

CROSS-REFERENCE TO RELATED APPLICATIONS

This application is a national stage application, filed under 35 U.S.C. §371, of International Application No. PCT/US2008/056403, filed on Mar. 10, 2008, which claims the benefit of and priority to U.S. Patent Application Ser. No. 60/900,558, filed Feb. 8, 2007, the disclosure of each is incorporated by reference herein.

Each of the applications and patents cited in this text, as well as each document or reference cited in each of the applications and patents (including during the prosecution of each issued patent; "application cited docutments"), and each of the U.S. and foreign applications or patents corresponding to and/or claiming priority from any of these applications and patents, and each of the documents cited or referenced in each of the application cited documents, are hereby expressly incorporated herein by reference. More generally, documents or references are cited in this text, either in a Reference List before the claims, or in the text itself; and, each of these documents or references ("herein-cited references"), as well as each document or reference cited in each of the herein-cited references (including any manufacturer's specifications, instructions, etc.), is hereby expressly incorporated herein by reference. Documents incorporated by reference into this text may be employed in practice of the invention.

RELATED APPLICATIONS

This application claims the benefit of priority to U.S. Provisional Patent Application Ser. No. 60/893,736, filed Mar. 8, 2007; which is hereby incorporated by reference in its entirety.

GOVERNMENT SUPPORT

This invention was made with support from the National Institutes of Health, NCI/NASA UIP, NIH NIDDK, NSF and DARPA-MTO; therefore, the government has certain rights in the invention.

BACKGROUND OF THE INVENTION

Mammalian cells in vivo integrate and respond to cues in their microenvironment that vary in both time and space. In particular, interactions between neighboring cells can regulate both the fate and function of individual cells as well as govern the emergent properties of the resultant tissue. Because such cell-cell interactions occur primarily through direct contact or exchange of soluble factors, understanding the temporal and spatial aspects of these signals is of fundamental importance to tissue biology. Recent advances in cell 'micropatterning' have already proven invaluable in increasing our understanding of the structure-function relationships of such multicellular communities (El-Ali, J., Sorger, P. K. & Jensen, K. F. (2006) *Nature* 442, 403-11; Bhatia, S. N., Balis, U. J., Yarmush, M. L. & Toner, M. (1999) *Faseb J* 13, 1883-900; Nelson, C. M., Jean, R. P., Tan, J. L., Liu, W. F., Sniadecki, N. J., Spector, A. A. & Chen, C. S. (2005) *Proc Natl Acad Sci USA* 102, 11594-9; and Liu, W. F., Nelson, C. M., Pirone, D. M. & Chen, C. S. (2006) *J. Cell Biol.* 173, 431-441). However, dynamic manipulation of tissue structure in vitro has remained largely out of reach.

Previous efforts towards spatio-temporal control of tissue organization at the cellular scale have focused on modulation of the adhesive properties of the culture substrate (Okano, T., Yamada, N., Okuhara, M., Sakai, H. & Sakurai, Y. (1995) *Biomaterials* 16, 297-303; Lahann, J., Mitragotri, S., Tran, T. N., Kaido, H., Sundaram, J., Choi, I. S., Hoffer, S., Somorjai, G. A. & Langer, R. (2003) *Science* 299, 371-4; and Jiang, X., Ferrigno, R., Mrksich, M. & Whitesides, G. M. (2003) *J Am Chem Soc* 125, 2366-7.). Through the micropatterning of surface chemistries that can be dynamically altered, localized attachment and release of cells has been demonstrated (Cheng, X. H., Wang, Y. B., Hanein, Y., Bohringer, K. F. & Ratner, B. D. (2004) *Journal of Biomedical Materials Research Part A* 70A, 159-168; and Yeo, W. S., Yousaf, M. N. & Mrksich, M. (2003) *J Am Chem Soc* 125, 14994-5). Nonetheless, these manipulations are typically not reversible (i.e., nonadhesive surfaces are rendered adhesive just once), they do not allow the decoupling of processes associated with adhesion from those correlated with cell-cell interaction (i.e., attachment, spreading, and contact with neighboring cells have overlapping time scales), nor can these platforms accommodate serial manipulations to mimic key biological events (i.e., sequential exposure of a target cell population to different inducer populations). Manipulations of surface chemistry are also limited by the inability to precisely control tissue composition: sequential seeding of different cell types can result in contamination of pure populations and maintaining micronscale proximity of two cell populations in the absence of contact over many days—important for decoupling the relative role of contact and paracrine signals—has not been achieved.

SUMMARY OF THE INVENTION

The development and function of living tissues depends largely on interactions between cells that can vary in both time and space; however, temporal control of cell-cell interaction is experimentally challenging. By employing a micromachined substrate with moving parts, herein is disclosed the dynamic regulation of cell-cell interactions via direct manipulation of adherent cells with micron-scale precision. The inventive devices and methods allow mechanical control of both tissue composition and spatial organization. The inventive device and methods enable the investigation of dynamic cell-cell interaction in a multitude of applications, such as intercellular communication, spanning embryogenesis, homeostasis, and pathogenic processes.

In one specific embodiment, the utility of the inventive devices and methods in deconstructing the dynamics of intercellular communication between hepatocytes and supportive stromal cells in co-culture is demonstrated. Specifically, the findings disclosed herein indicate that the maintenance of the hepatocellular phenotype by stroma requires direct contact for a limited time (on the order of hours) followed by a sustained soluble signal which has an effective range of less than about 400 µm.

In another embodiment, use of the inventive devices and methods to characterize the microenvironmental regulation of sinusoidal endothelial cell phenotypes is demonstrated. Specifically, disclosed are novel microenvironmental regulators of the liver sinusoidal endothelial cells (LSEC) phenotype, which may be important for the development of better in vitro models of liver disease.

BRIEF DESCRIPTION OF THE FIGURES

FIGS. 8a and 8b depict a table of Selected Immune Cytokines and Their Activities. Key: CTL: cytotoxic T lymphocytes; DC: dendritic cells; GM-CSF: Granulocyte-Monocyte Colony Stimulating Factor; IL: interleukin; IFN: Interferon; TGF: Tumor Growth Factor; TNF: Tumor Necrosis Factor. Note that "*" indicates that italicized activities are inhibited.

FIG. 9 depicts data showing that LSEC lose their differentiated phenotype when cultured ex vivo. (A) Specifically, there is a strong decrease in the LSEC-specific marker SE-1 and an increase in the non-specific endothelial marker PECAM-1, comparing cells at 1 day versus 3 days of culture. There is no significant change in RECA observed. (B) In vivo, SE-1 is shown to mark the cells in the sinusoidal vascular endothelium, the site of the LSEC. PECAM-1 is shown to mark cells in larger diameter blood vessels, the site of vascular endothelial cells.

FIG. 12 depicts examples of molds for casting polymer replicas of the microfabricated silicon parts. (A) PDMS mold cast from one embodiment of a comb component of the invention. (B) Silicon wafer parts from which device elements have been cut are reassembled on a PDMS base to form a cavity in which replica parts may be cast.

FIG. 13 depicts population-specific readout or selective interrogation. Hepatocytes and 3T3 fibroblasts are co-cultured to maintain hepatocyte differentiation. In (A) the drug Pyrilamine is introduced while the cells are in co-culture. By using the micromechanical substrates, the two cell populations are separated prior to viability assay, allowing the viability of each cell type to be assessed independently. The 3T3 are shown to be more sensitive to the toxic effects of Pyrilamine. In (B) the effect of the drug Methapyrilamine is compared when the cells are in co-culture or when the 3T3 are alone. The 3T3 are shown to be more sensitive to the toxic effects of the drug when alone.

DETAILED DESCRIPTION OF THE INVENTION

Figure 1:
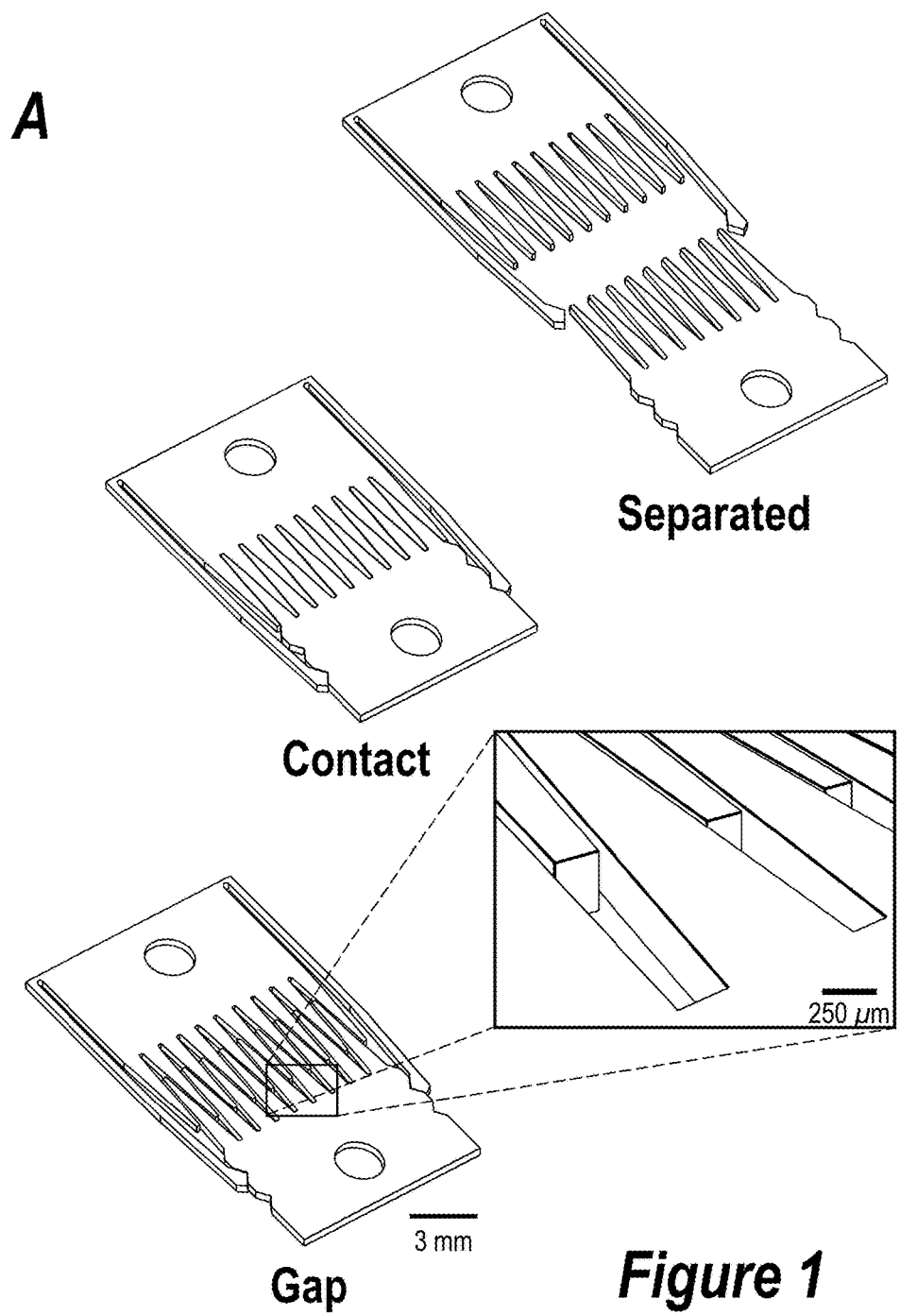
FIG. 1 depicts micromechanical substrates which enable micrometer-resolution cell positioning. (A) Microfabricated silicon parts can be fully separated (left), or locked together with comb fingers in contact (middle) or slightly separated (right). Cells are cultured on the top surfaces; manual scraping can be used to restrict cells to the comb fingers only (inset). The slope of the tapered comb fingers results in a 20:1 mechanical transmission ratio; that is, sliding the parts 1.6 mm changes the gap between the fingers by only 80 μm. Together with the integrated snap-lock mechanism, it is thereby possible to control separation with repeatable micrometer-scale precision using unassisted manual actuation. (B and C) Brightfield images of hepatocytes (darker cells) and 3T3 fibroblasts cultured on the comb fingers. The silicon is first functionalized by spin-coating with polystyrene followed by plasma treatment, resulting in a surface comparable to tissue culture plastic. Devices can be reused multiple times (>20). (D) Devices in a standard 12-well plate. Cell culture and functional assays are performed using standard methods. Actuation is also performed directly on the plate using sterile tweezers. (E) One embodiment of micromechanical substrates which enable micrometer-resolution cell positioning.
Figure 1:
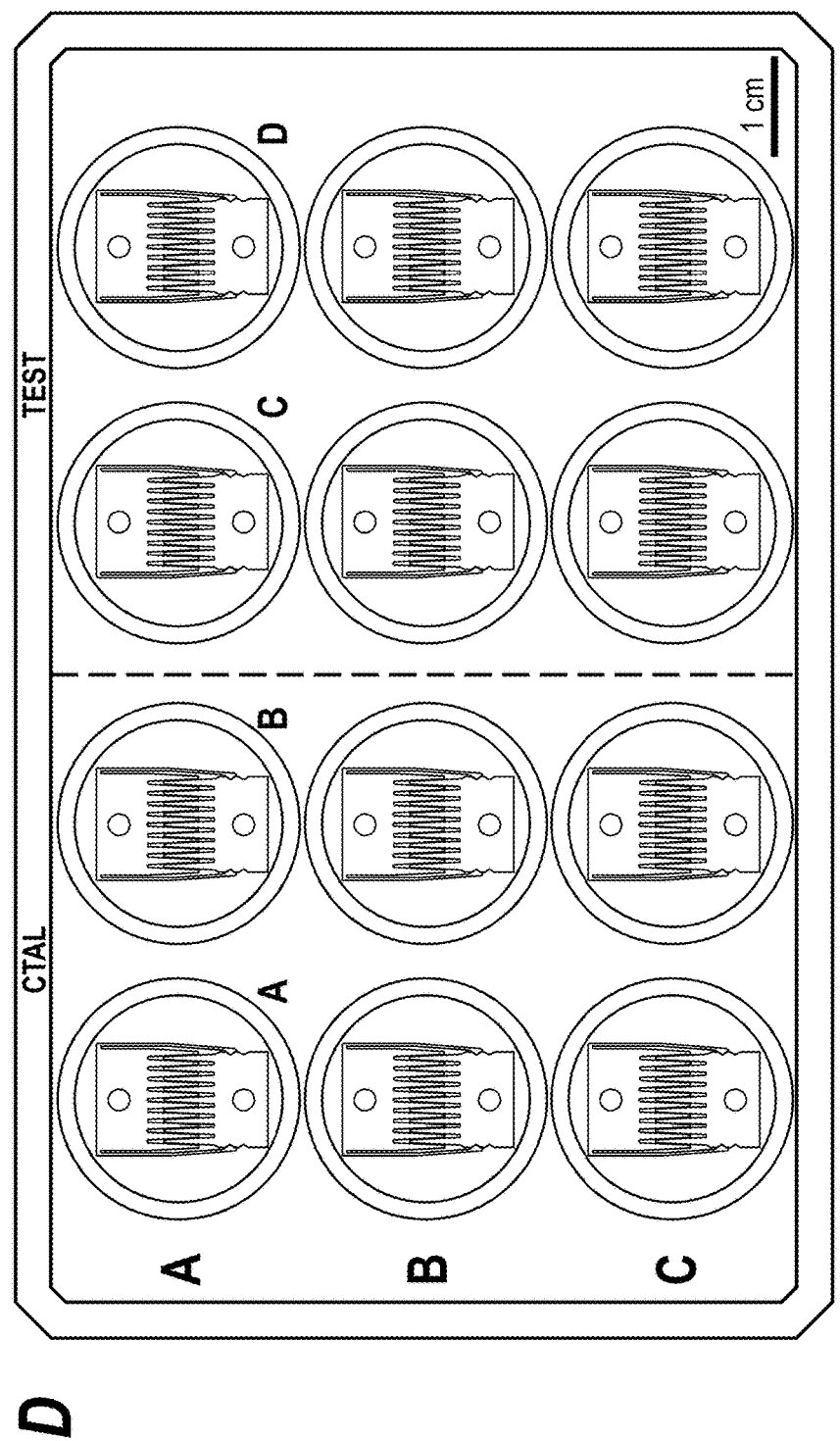
Figure 1:
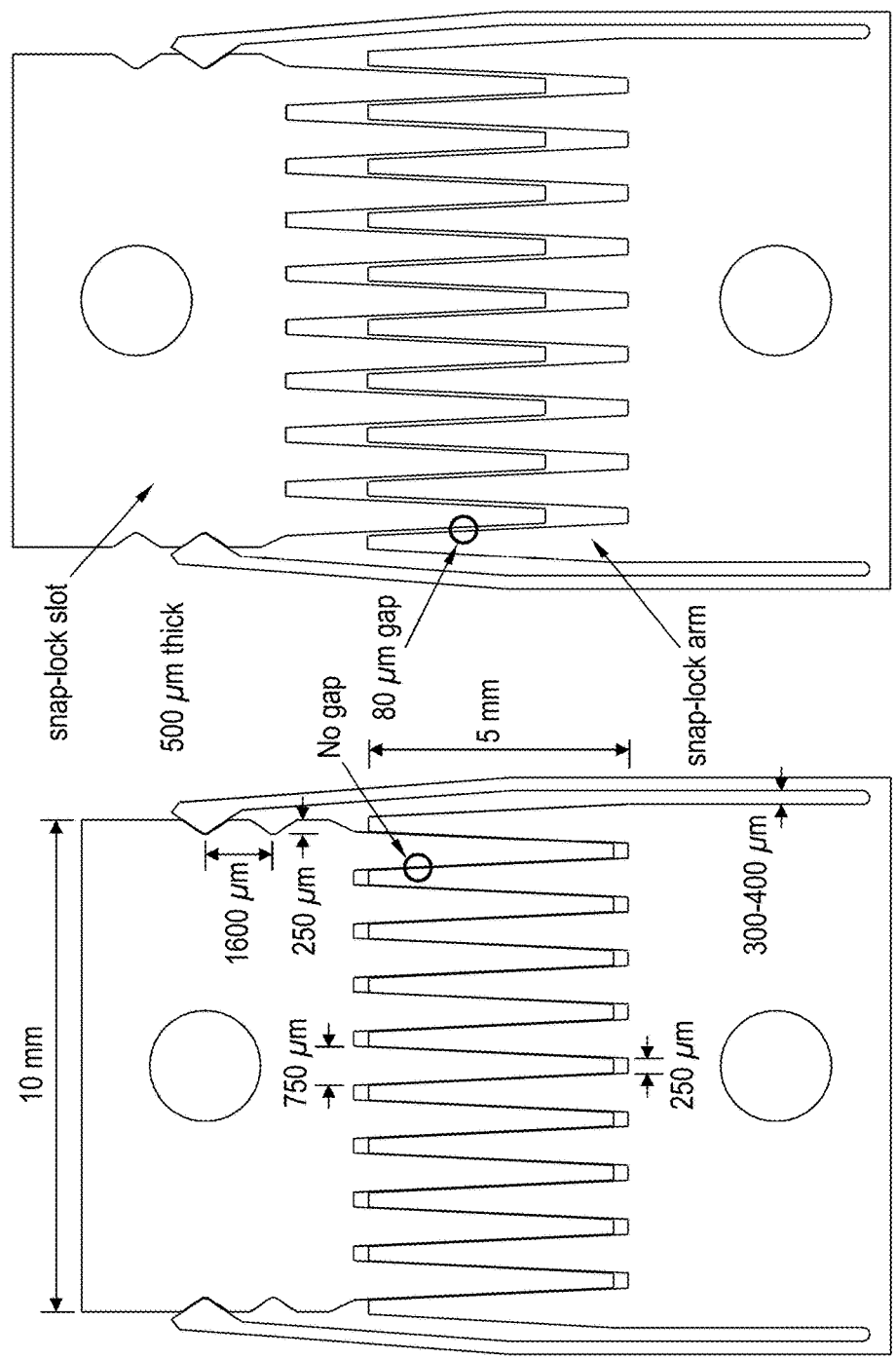

Overview. Cellular behavior within tissues is driven by environmental cues that vary temporally and spatially with a granularity on the order of individual cells. Local cell-cell interactions via secreted and contact-mediated signals play a critical role in these pathways. In order to study these dynamic small-scale processes, herein is disclosed a micromechanical platform to control microscale cell organization so that cell patterns can be reconfigured dynamically. In one embodiment, this tool has been employed to deconstruct the mechanisms by which liver-specific function is maintained in hepatocytes upon co-cultivation with stromal support cells. Specifically, the relative roles of cell contact and short-range soluble signals, duration of contact, and the possibility of bi-directional signaling were examined. In another embodiment, this tool has been used to investigated microenvironmental regulation of the sinusoidal endothelial cell phenotype.

In certain embodiments, the inventive device consists of two parts that can be locked together either to allow cell-cell contact across the two parts or to separate the cells by a uniform gap. Switching between these two states is actuated simply by pushing the parts manually using tweezers; no micromanipulation machinery is necessary. Micron-scale precision is possible due to a 20:1 mechanical transmission ratio and microfabricated snap locks, both of which are monolithically incorporated into the silicon structure. In certain embodiments, the entire device is fabricated in a simple single-mask process using through-wafer deep reactive ion etching. In certain embodiments, to provide a surface compatible with cell culture, the surface is coated with a layer of polystyrene and plasma-treated, providing a standard tissue-culture surface. In other embodiments, the device is fabricated from silicon. In other embodiments, the device is fabricated from polyurethane. In certain embodiments, the parts can be anchored to a frame while being etched, and then released with a dicing saw or the like.

Herein are disclosed devices and methods designed to enable one precisely to control tissue organization and composition by leveraging tools from the field of micro-electromechanical systems (MEMS), which offers precise physical manipulation at a length scale comparable to that of many biological processes. In certain embodiments, cells are grown on an array of micromachined plates that are physically rearranged in order to change the spatial organization of the culture. This will be referred to as micromechanical reconfigurable culture (µRC). Cells remain attached to the substrate throughout the repositioning process (Chen, C. S., Mrksich, M., Huang, S., Whitesides, G. M. & Ingber, D. E. (1997) Science 276, 1425-1428; and McBeath, R., Pirone, D. M., Nelson, C. M., Bhadriraju, K. & Chen, C. S. (2004) Dev Cell 6, 483-95). Using µRC, dynamic regulation of cell-cell interactions via direct manipulation of cell positioning has been demonstrated. Specifically, cell-cell contact between different cell populations was regulated by positioning plates together or apart. By imposing a small micron-scale separation between the plates, cell-cell contact can be abrogated while soluble signaling is maintained. By employing larger separation distances, the extent of soluble signaling can also be modulated. In addition, by removing a plate and replacing it, one population of cells can be exchanged for another in a modular fashion. Thus, this MEMS-based approach provides dynamic control of both tissue organization and composition.

Micromechanical Reconfigurable Culture Devices (µRC). In certain embodiments, the micromechanical reconfigurable culture devices of the invention consist of two or more components that can be moved with respect to each other. In certain embodiments, the devices of the invention are a single piece, parts of which can be moved with respect to each other. In certain embodiments, the components of the device are shaped as flat plates or curved surfaces.

In certain embodiments, the components of the device can be mounted on a positioning system which allows their position, relative to each other, to be varied. In another embodiment, in order to connect the two (or more) component, one or more flexures may be used. As used herein, a "flexure" is a flexible mechanical member used to connect two separate components. A properly designed flexure is extremely stiff in every direction except the direction of motion. In certain embodiments, the flexures of the invention may be used as a hinge to guide the linear motion of two or more of the components.

In certain embodiments, at least one of the components of the device will have two substantially-parallel arm flexures protruding from the main body of the component. In certain embodiments, these arm flexures each include a distal catch (or latch) with corresponds to slot (or notch) on a separate component. An example of the use of flexures in the invention is the integrated snap-lock mechanism shown in FIG. 1E. As shown in FIG. 1E, in certain embodiments, the matching V-shaped latches and notches are self-centering, allowing the parts to be accurately and reproducibly positioned using only tweezers, without the need for microscopic visualization or micromanipulation machinery. In certain embodiments, the extent of finger separation in the gap mode can be tuned via notch positioning; multiple sets of notches could also be employed to allow variable spacing.

In certain embodiments, the snap-lock mechanism can consist of more than one set of snaps and slots, giving multiple points of constraint (e.g., leading to greater stability). In certain embodiments, there are two snaps and two sets of locks.

Further, the alignment of components of the invention may be facilitated by features on one component which fit into features of another component, thereby constraining the mechanical positioning of the components. For example, in certain embodiments, these features are implemented as teeth in a comb pattern. In certain embodiments, the contacting surfaces are angled with respect to the direction of motion so that the changes in separation between parts is less than the total amount of motion. In such embodiments, finer positioning accuracy can be obtained, particularly when using coarse actualization methods, such as manual pushing.

In certain embodiments, the μRC device consists of two components with interlocking comb fingers and an integrated snap-lock mechanism (as discussed above). The components can be fully separated, locked together with the fingers in contact, or locked together with a fixed gap between the comb fingers (FIG. 1A). These configurations are referred to as the separated, contact, and gap modes. Cells are cultured on the top surface of the fingers (FIGS. 1B and 1C). In certain embodiments, each the fingers of each component can contain one type of cell, wherein the cells on the first component are not the same as the cells on the second component. In other words, each component has a "pure" population of cells. In other embodiments, the cells cultured on any given finger can be a mixed population of more than one cell type.

In certain embodiments, parts can be separated into individual wells of a multi-well plate for coating of extracellular matrix proteins and seeding of cells, so as to avoid cross-contamination. Following cell attachment, the two parts can be assembled in a fresh well (FIG. 1D), where cell culture and functional assays can be performed in a standard manner. The actuation strategy to switch between modes was designed for simplicity and compatibility with standard aseptic cell-culture technique.

Figure 7:
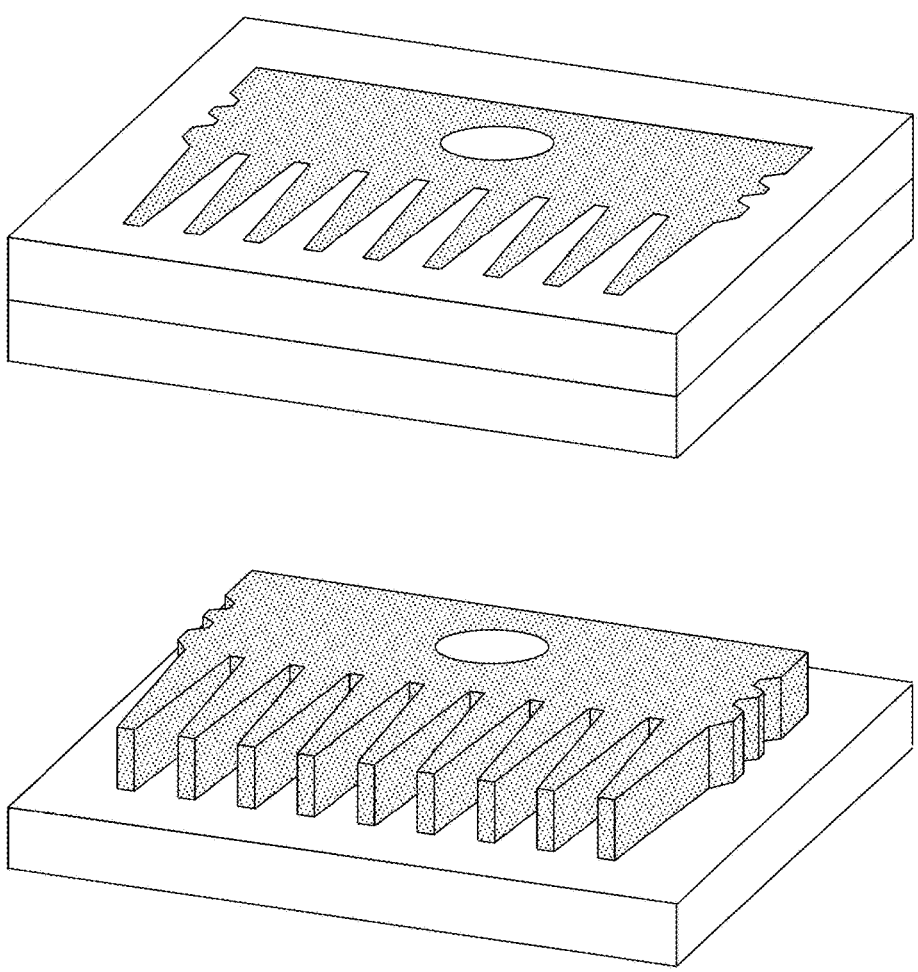
FIG. 7 depicts intermediates in one approach to device fabrication.

In certain embodiments, the entire μRC device is fabricated in a simple single-mask process using through-wafer deep reactive ion etching (see intermediates of this process in FIG. 7). See, for example: Ayon, A. A., Braff, R., Lin, C. C., Sawin, H. H. & Schmidt, M. A. (1999) *Journal of the Electrochemical Society* 146, 339-349; and Knobloch, A. J., Wasilik, M., Fernandez-Pello, C. & Pisano, A. P. (2003) in 2003 *ASME International Mechanical Engineering Congress* (American Society of Mechanical Engineers, New York, N.Y. 10016-5990, United States, Washington, D.C., United States), Vol. 5, pp. 115-123. In certain embodiments, a silicon wafer can be coated with a micrometer thick layer of silicon dioxide. After which, a layer of thick photoresist can be spin-coated onto the coated silicon wafer, patterned using a chrome mask and contact alignment, and developed. The patterned wafer, or device wafer, can then be attached to a handle wafer using a photoresist bond. After etching through the oxide layer, deep reactive ion etching can be used to etch through the entire device wafer. The parts can then be released in acetone and cleaned in "Piranha" (chromic acid-containing) solution.

Figure 2:
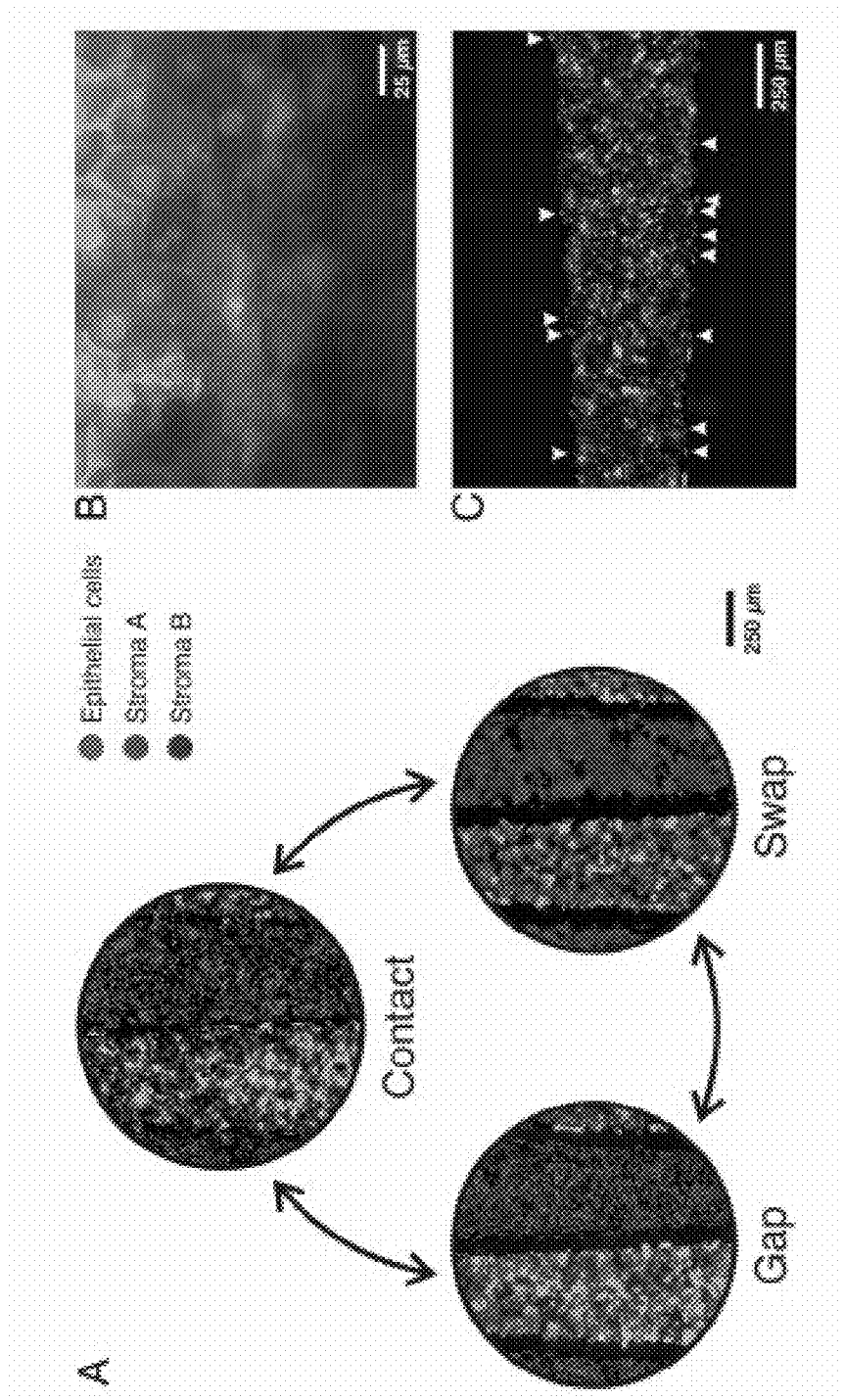
FIG. 2 depicts the results of reconfigurable cell culture studies. Cultures can be reversibly switched to initiate or to eliminate contact between two cell populations; individual populations can also be removed and replaced. (A) Fluorescent images illustrating possible device manipulations. Each cell type was pre-labeled with an individual dye color. (B) Fluorescent image showing intimate contact between hepatocytes (green) and stroma (red, 3T3 fibroblasts) at the interface between neighboring comb fingers. Image was taken 18 h following initiation of contact. Cell nuclei counterstained in blue. (C) Cross-migration of cells is minimal for moderate durations of contact. Representative fluorescent image showing small numbers of stromal cells (red, arrows indicate selected cells) remaining behind on a hepatocyte finger (green) after combs were separated following 18 h of contact. In this work, contact was limited to 18 h in order to minimize cross-migration, but longer durations are possible with other cell types (data not shown).

As mentioned above, to provide the necessary mechanical precision, silicon parts can be fabricated in a single mask, through-wafer, deep reactive ion etching process. In the exemplification provided herein, a separation of 6 μm or less was measured in the contact mode, and 79±1 μm in the gap mode. Using fluorescent membrane dyes and microscopy, cells on opposing fingers were shown to form intimate contacts in contact mode (FIG. 2B). In addition, contamination of cells between adjacent fingers after 18 hours of contact was minimal (FIG. 2C).

In certain embodiments, the silicon parts of the μRC device are modified to aid in the culture of different cell types. In certain embodiment, the silicon parts of the device spincoated with polystyrene, resulting in a surface comparable to tissue culture plastic. This can aid, for example, in the binding of fibroblasts; poor adhesion was of fibroblast cells on unmodified silicon surfaces has been observed (data not shown). In certain embodiments, collagen is adsorbed onto the silicon parts of the device. This can aid, for example, in the binding of hepatocytes.

In certain embodiments, the inventive μRC device could include embedded microfluidics and sensors for local delivery of soluble factors and in situ monitoring (Papageorgiou, D. P., Shore, S. E., Bledsoe Jr, S. C. & Wise, K. D. (2006) *Journal of Microelectromechanical Systems* 15, 1025-1033), and/or integrated actuation for heterogeneous mechanical control of array elements.

In certain embodiments, the μRC device is fabricated from an optically transparent material. In certain embodiments, the μRC device is fabricated from an optically translucent material. Transparent and translucent μRC devices could be used with inverted biological microscopes. As used herein, transparent materials can be seen through; that is, they allow clear images to pass. Translucent materials allow light to pass through them only diffusely, that is, the material distorts the image. In certain embodiments, the μRC device is fabricated from an optically transparent or optically translucent material selected from the group consisting of glasses and plastics.

In certain embodiments, the μRC device comprises more than two interlocking pieces. In certain embodiments, the μRC device comprises more three interlocking pieces. In certain embodiments, the μRC device comprises four interlocking pieces. In certain embodiments, the μRC device comprises more than four interlocking pieces.

Developmental Biology: Stem Cells/Morphogens. Cell-cell interactions play a critical role in driving differentiation during development. Stem cells are defined as cells that are capable of a differentiation into many other differentiated cell types. Embryonic stem cells are stem cells from embryos which are capable of differentiation into most, if not all, of the differentiated cell types of a mature body. Stem cells are referred to as pluripotent, which describes this capability of differentiating into many cell types. A category of pluripotent stem cell of high interest to the research community is the human embryonic stem cell, abbreviated here as hES cell, which is an embryonic stem cell derived from a human embryonic source. Human embryonic stem cells are of great scientific interest because they are capable of indefinite proliferation in culture and are thus capable, at least in principle, of supplying cells and tissues for replacement of failing or defective human tissue. The existence in culture of human embryonic stem cells offers the potential of unlimited amounts of human cells and tissues for use in a variety of therapeutic protocols to assist in human health. In the future human embryonic stem cells may be proliferated and directed to differentiate into specific lineages so as to develop differentiated cells or tissues which can be transplanted into human bodies for therapeutic purposes.

One of most significant features of human embryonic stem cells is the attribute of being capable of self-renewal. By that, it is meant that the hES cells are capable of proliferating into multiple progeny stem cells, each of which seems to have the full potential of its ancestor cell. In other words, the progeny are renewed to have all the developmental and proliferative capacity of the parental cell. This attribute, combined with the pluripotency, are the traits that make hES cells candidates for many potential uses, since, in theory, hES cells can be reproduced indefinitely and in large numbers and then induced to become any cell type in the human body. The ability to self-renew appears closely linked to the attribute of being undifferentiated in the sense that at least given present knowledge, only undifferentiated hES cells are capable of indefinite self-renewal; i.e., as soon as the cells differentiate, the self-renewal capability is lost.

During the course of development, cells of many tissues differentiate according to the positional information that is set by the concentration gradients of morphogens. Morphogens are signaling molecules that emanate from a restricted region of a tissue and spread away from their source to form a concentration gradient. As the fate of each cell in the field depends on the concentration of the morphogen signal, the gradient prefigures the pattern of development. Thus, micromechanical reconfigurable culture (μRC) is an ideal way to study morphogens and the cells they effect (e.g., stem cells).

As described above, a morphogen is a substance governing the pattern of tissue development and, in particular, the positions of the various specialized cell types within a tissue. It spreads from a localized source and forms a concentration gradient across a developing tissue. Well-known morphogens include: Decapentaplegic/Transforming growth factor beta, Hedgehog/Sonic Hedgehog, Wingless/Wnt, Epidermal growth factor, and Fibroblast growth factor. Morphogens are defined conceptually, not chemically, so simple chemicals such as retinoic acid may also act as morphogens.

For example, bone morphogenesis is induced by bone morphogenetic proteins (BMPs). BMPs play a role in pattern formation, cell differentiation, maintenance and regeneration of tissues. BMPs are pleiotropic and act on chemotaxis, mitosis and differentiation of progenitor stem cells. There are nearly twenty BMPs in the human genome. BMPs have actions beyond bone in development of teeth, heart, kidney, eye, skin, and brain. Thus, BMPs may be called body morphogenetic proteins. Stem cells are primordial cells with unlimited replicative potential and can be programmed by morphogens such as BMPs.

Developmental Biology: Cytokines/Cytokine Receptors. Cytokines are small secreted proteins which mediate and regulate immunity, inflammation, and hematopoiesis. They often are produced de novo in response to an immune stimulus. They generally (although not always) act over short distances and short time spans and at very low concentration. They act by binding to specific membrane receptors, which then signal the cell via second messengers, often tyrosine kinases, to alter its behavior (gene expression). Responses to cytokines include increasing or decreasing expression of membrane proteins (including cytokine receptors), proliferation, and secretion of effector molecules. Thus, micromechanical reconfigurable culture (μRC) is an ideal way to study cytokines and their receptors.

Cytokine is a general name; other names include lymphokine (cytokines made by lymphocytes), monokine (cytokines made by monocytes), chemokine (cytokines with chemotactic activities), and interleukin (cytokines made by one leukocyte and acting on other leukocytes). Cytokines may act on the cells that secrete them (autocrine action), on nearby cells (paracrine action), or in some instances on distant cells (endocrine action). As used herein, cytokine encompasses all of these.

It is common for different cell types to secrete the same cytokine or for a single cytokine to act on several different cell types (pleiotropy; see FIGS. 8a and 8b). Cytokines are redundant in their activity, meaning similar functions can be stimulated by different cytokines. Cytokines are often produced in a cascade, as one cytokine stimulates its target cells to make additional cytokines. Cytokines can also act synergistically (two or more cytokines acting together) or antagonistically (cytokines causing opposing activities).

Their short half life, low plasma concentrations, pleiotropy, and redundancy all complicated the isolation and characterization of cytokines. Searches for new cytokines is now often conducted at the DNA level, identifying genes similar to known cytokine genes. However, micromechanical reconfigurable culture (μRC) might allow an alternative way in which to identify new cytokines, as well as study the effects of known cytokines.

The largest group of cytokines stimulates immune cell proliferation and differentiation. This group includes Interleukin 1 (IL-1), which activates T cells; IL-2, which stimulates proliferation of antigen-activated T and B cells; IL-4, IL-5, and IL-6, which stimulate proliferation and differentiation of B cells; Interferon gamma (IFNg), which activates macrophages; and IL-3, IL-7 and Granulocyte Monocyte Colony-Stimulating Factor (GM-CSF), which stimulate hematopoiesis.

Other groups of cytokines include interferons and chemokines. Interferons IFNa and IFNb inhibit virus replication in infected cells, while IFNg also stimulates antigen-presenting cell MHC expression. Chemokines attract leukocytes to infection sites. Chemokines have conserved cysteine residues that allow them to be assigned to four groups. The groups, with representative chemokines, are C-C chemokines (RANTES, MCP-1, MIP-1a, and MIP-1b), C-X-C chemokines (IL-8), C chemokines (Lymphotactin), and CXXXC chemokines (Fractalkine). Some cytokines are predominantly inhibitory. For example, IL-10 and IL-13 inhibit inflammatory cytokine production by macrophages.

Helper T cells have two important functions: to stimulate cellular immunity and inflammation, and to stimulate B cells to produce antibody. Two functionally distinct subsets of T cells secrete cytokines which promote these different activities. Th1 cells produce IL-2, IFNγ, and TNFβ, which activate Tc and macrophages to stimulate cellular immunity and inflammation. Th1 cells also secrete IL-3 and GM-CSF to stimulate the bone marrow to produce more leukocytes. Th2 cells secrete IL-4, IL-5, IL-6, and IL-10, which stimulate antibody production by B cells.

T cells are initially activated as Th0 cells, which produce IL-2, IL-4 and IFNγ. The nearby cytokine environment then influences differentiation into Th1 or Th2 cells. IL-4 stimulates Th2 activity and suppresses Th1 activity, while IL-12 promotes Th1 activities. Th1 and Th2 cytokines are antagonistic in activity. Th1 cytokine IFNg inhibits proliferation of Th2 cells, while IFNγ and IL-2 stimulate B cells to secrete $IgG_{2a}$ and inhibit secretion of $IgG_1$ and IgE. Th2 cytokine IL-10 inhibits Th1 secretion of IFNg and IL-2; it also suppresses Class II MHC expression and production of bacterial killing molecules and inflammatory cytokines by macrophages. IL-4 stimulates B cells to secrete IgE and $IgG_1$. The balance between Th1 and Th2 activity may steer the immune response in the direction of cell-mediated or humoral immunity.

Cytokines act on their target cells by binding specific membrane receptors. The receptors and their corresponding cytokines have been divided into several families based on their structure and activities. Hematopoietin family receptors are dimers or trimers with conserved cysteines in their extracellular domains and a conserved Trp-Ser-X-Trp-Ser sequence. Examples are receptors for IL-2 through IL-7 and GM-CSF. Interferon family receptors have the conserved cysteine residues but not the Trp-Ser-X-Trp-Ser sequence, and include the receptors for IFNα, IFNβ, and IFNγ. Tumor Necrosis Factor family receptors have four extracellular domains; they include receptors for soluble TNFα and TNFβ as well as membrane-bound CD40 (important for B cell and macrophage activation) and Fas (which signals the cell to undergo apoptosis). Chemokine family receptors have seven transmembrane helices and interact with G protein. This family includes receptors for IL-8, MIP-1 and RANTES. Chemokine receptors CCR5 and CXCR4 are used by HIV to preferentially enter either macrophages or T cells.

Hematopoietin cytokine receptors are the best characterized. They generally have two subunits, one cytokine-specific and one signal transducing. An example is the GM-CSF subfamily, where a unique a subunit specifically binds either GM-CSF, IL-3, or IL-5 with low affinity and a shared β subunit signal transducer also increases cytokine-binding affinity. Cytokine binding promotes dimerization of the α and β subunits, which then associate with cytoplasmic tyrosine kinases to phosphorylate proteins which activate mRNA transcription. GM-CSF and IL-3 act on hematopoietic stem cells and progenitor cells and activate monocytes. With IL-5, they also stimulate eosinophil proliferation and basophil degranulation. All three receptors phosphorylate the same cytoplasmic protein. Antagonistic GM-CSF and IL-3 activities can be explained by their competition for limited amounts of β subunit.

The IL-2R subfamily of receptors for IL-2, IL-4, IL-7, IL-9, and IL-15 have a common signal-transducing g chain. Each has a unique cytokine-specific a chain. IL-2 and IL-15 are trimers, and share an IL-2R β chain. Monomeric IL-2R a has low affinity for IL-2, dimeric IL-2R bg has intermediate affinity, and trimeric IL-2R abg binds IL-2 with high affinity. IL-2R α chain (Tac) is expressed by activated but not resting T cells. Resting T cells and NK cells constitutively express low numbers of IL-2βγ. Antigen activation stimulates T cell expression of high affinity IL-2R trimers as well as secretion of IL-2, allowing autocrine stimulation of T cell proliferation in an antigen-specific manner. Antigen specificity of the immune response is also maintained by the close proximity of antigen-presenting B cells and macrophages with their helper T cells, so that cytokines are secreted in the direction and close to the membrane of the target cell. X-linked severe combined immunodeficiency (X-scid) is caused by a defect in IL-2R family γ chain, which results in loss of activity from this family of cytokines.

Cytokine activity can be blocked by antagonists, molecules which bind cytokines or their receptors. IL-1 has a specific antagonist that blocks binding of IL-1α and IL-1β to their receptor. During immune responses, fragments of membrane receptors may be shed and then compete for cytokine binding. Microbes also influence cytokine activities. For example, Vaccinia virus (Smallpox and Cowpox) encodes soluble molecules which bind IFNγ, while Epstein-Barr virus (Infectious Mononucleosis) encodes a molecule homologous to IL-10 that suppresses immune function in the host.

The TNF receptor family molecules CD40 and Fas bind cell surface ligands on effector T cells: CD40L and FasL. CD40 is expressed on B cell and macrophage plasma membranes. T cell CD40L binding to B cell CD40 stimulates B cell proliferation and isotype switching. T cell CD40L binding to macrophage CD40 stimulates macrophages to secrete TNFa and become much more sensitive to IFNγ. T cell FasL binding to Fas leads to the activation of caspase proteases that initiate apoptosis of the cell expressing membrane Fas. Activated lymphocytes express Fas, so that FasL-positive Tc cells can regulate the immune response by eliminating activated cells. An immune deficiency disease linked to expression of a mutant Fas is characterized by over-proliferation of lymphocytes.

Cancer Biology. Interactions between a tumor and its surrounding stroma are known to play an important role in determining the progression of certain cancers. Cancers are classified by the type of cell that resembles the tumor and, therefore, the tissue presumed to be the origin of the tumor. The following general categories are usually accepted: carcinoma, lymphomas, leukemias, sarcomas, mesotheliomas, gliomas, germinomas, and choriocarcinomas. Carcinomas are malignant tumors derived from epithelial cells. This group represent the most common cancers, including the common forms of breast, prostate, lung and colon cancer. Lymphomas and leukemias are malignant tumors derived from blood and bone marrow cells. Sarcomas are malignant tumors derived from connective tissue, or mesenchymal cells. Mesotheliomas are tumors derived from the mesothelial cells lining the peritoneum and the pleura. Gliomas are tumors derived from glia, the most common type of brain cell. Germinomas are tumors derived from germ cells, normally found in the testicle and ovary. Choriocarcinomas are malignant tumors derived from the placenta.

RNAi. In certain embodiments of the invention, RNA interference (RNAi) techniques can be used in conjunction with method which employ the micromechanical reconfigurable culture devices of the invention. RNAi is a technique widely used to down-regulate the mRNA level of a specific gene. Small interfering RNAs (siRNAs) or small hairpin RNAs (shRNAs) are composed of a 22 nt-double strand RNA sequence completely homologous to an unique target gene. ShRNAs are generally produced by RNA polymerase II or III-based vectors while siRNA can be obtained from biotechnology companies. The siRNA or shRNA-expressing vectors are transfected into cell lines with classical lipotransfectants. The homology of sequence with a specific target gene allows formation of a complex comprising one strand of the shRNA or siRNA hybridized with the mRNA target and the RISC (RNAi-induced silencing complex) proteins in the cytoplasm. RISC then degrades the mRNA, which cannot be translated. The whole process leads to the specific downregulation of the RNA of the corresponding gene within 24-72 hours.

Microenvironmental Regulation of Sinusoidal Endothelial Cell Phenotypes. Liver Sinusoidal Endothelial Cells (LSEC) are distinct from other vascular endothelial cells (EC) present in other tissues in their structural and functional phenotypic characteristics. For example, in contrast to other EC, LSEC display fenestrations, have low or absent expression of PECAM-1, and in rat tissue, they distinctively express the specific surface marker SE-1. Interestingly, these phenotypic characteristics are lost over time when LSEC are placed in culture. Since phenotypic maintenance is critical to the development of accurate in vitro liver models and tissue engineered constructs, by using the devices and methods described herein the one can examine effect of various microenvironmental stimuli, such as tailoring of the extracellular matrix (ECM) and co-culture with supportive cell types, on LSEC phenotype.

Figure 10:
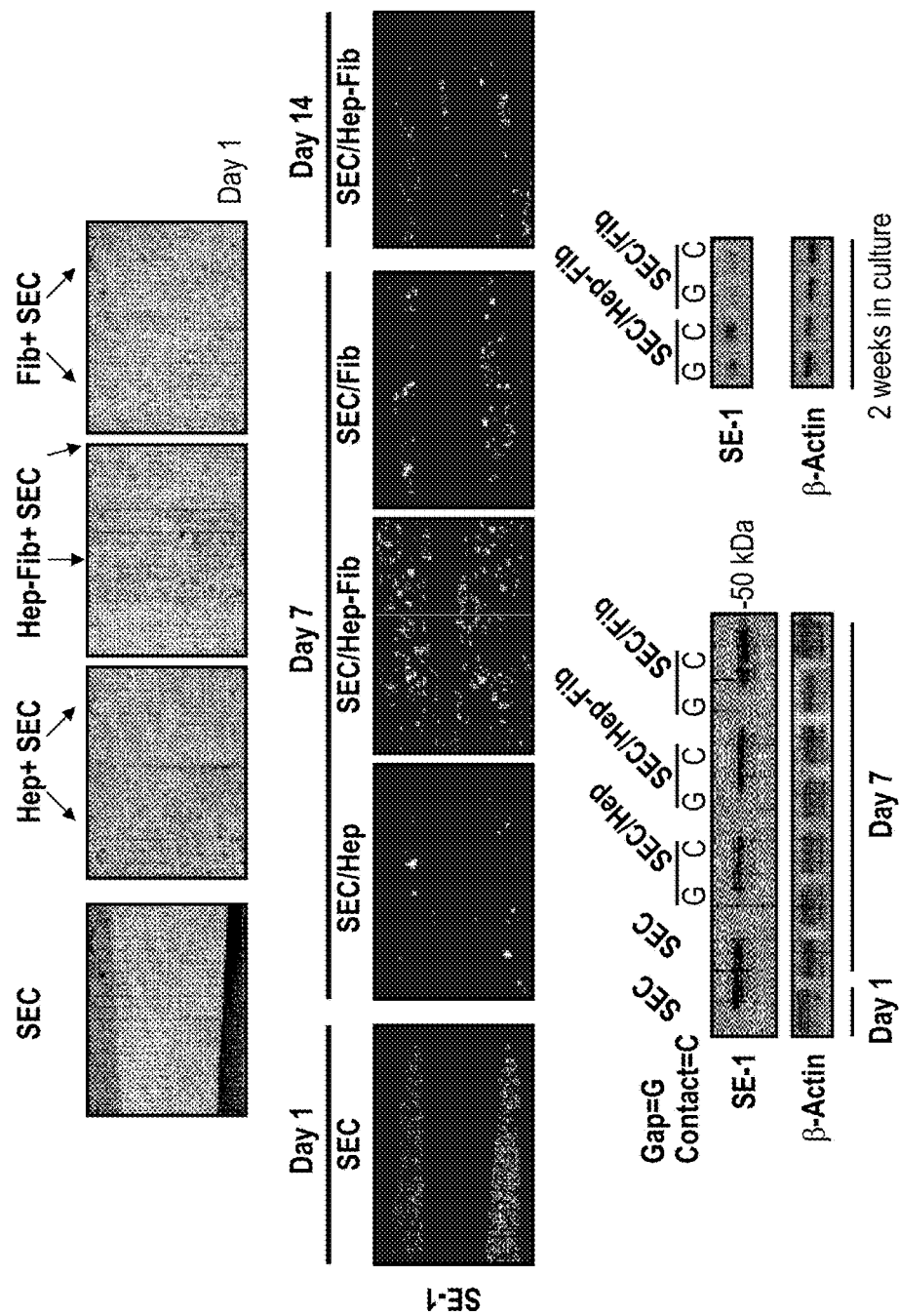
FIG. 10 depicts data showing that LSEC, when in co-culture with supportive cell types, can maintain their differentiated phenotype (expression of SE-1) for up to 14 days. The optimum maintenance is obtained in the case where LSEC are cultured with both hepatocytes and 3T3 fibroblasts together. This is demonstrated by immunofluorescence (top) as well as by Western Blot (bottom). Direct cell-cell contact did not appear to be necessary for maintenance of SE-1 expression (bottom). (Top) Use of the micromechanical substrates enables organization of the cell types to facilitate identification during microscopy. (Bottom) Use of the micromechanical substrates enables LSEC to be separated from the support cells prior to Western Blot analysis, resulting in a clean measurement from a purified cell population.
Figure 11:
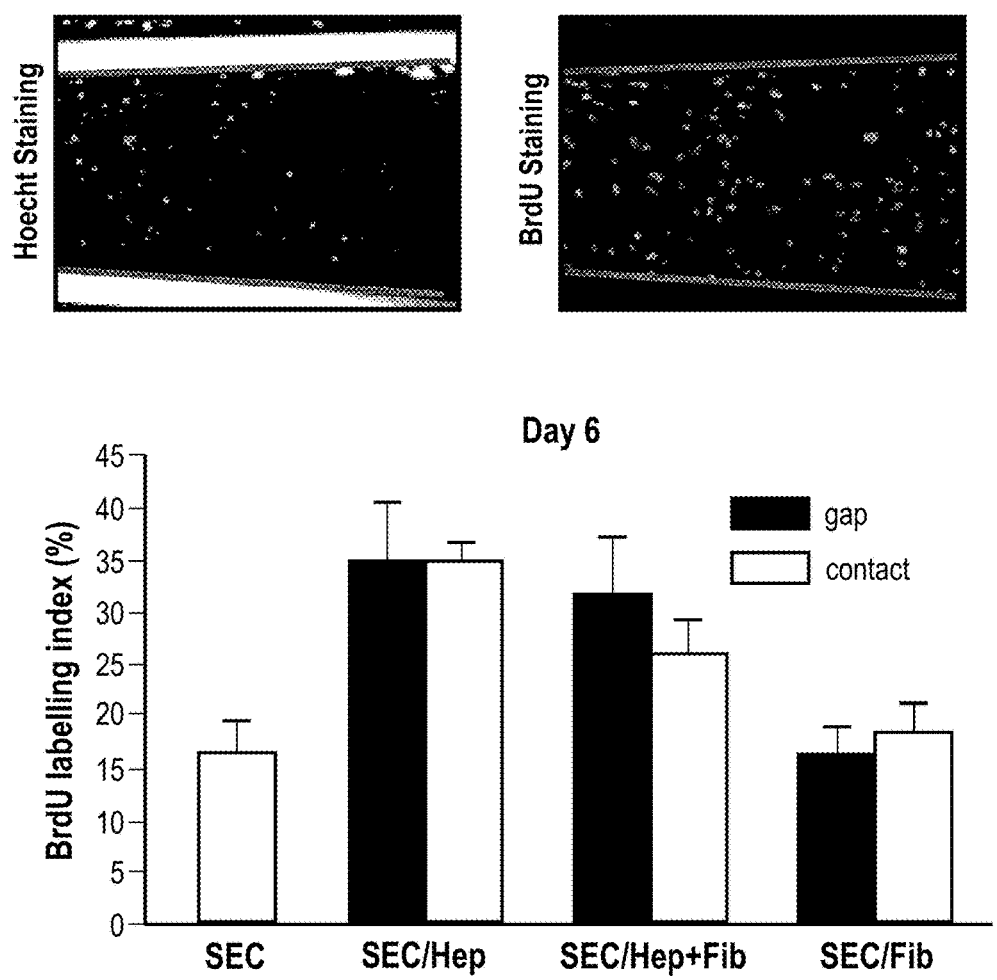
FIG. 11 depicts data showing LSEC proliferation as a function of various supportive cell types in co-culture. Maximum proliferation is obtained in co-culture with hepatocytes (either alone or together with 3T3 fibroblasts). Proliferation is measured via incorporation of BrdU.
Figure 14:
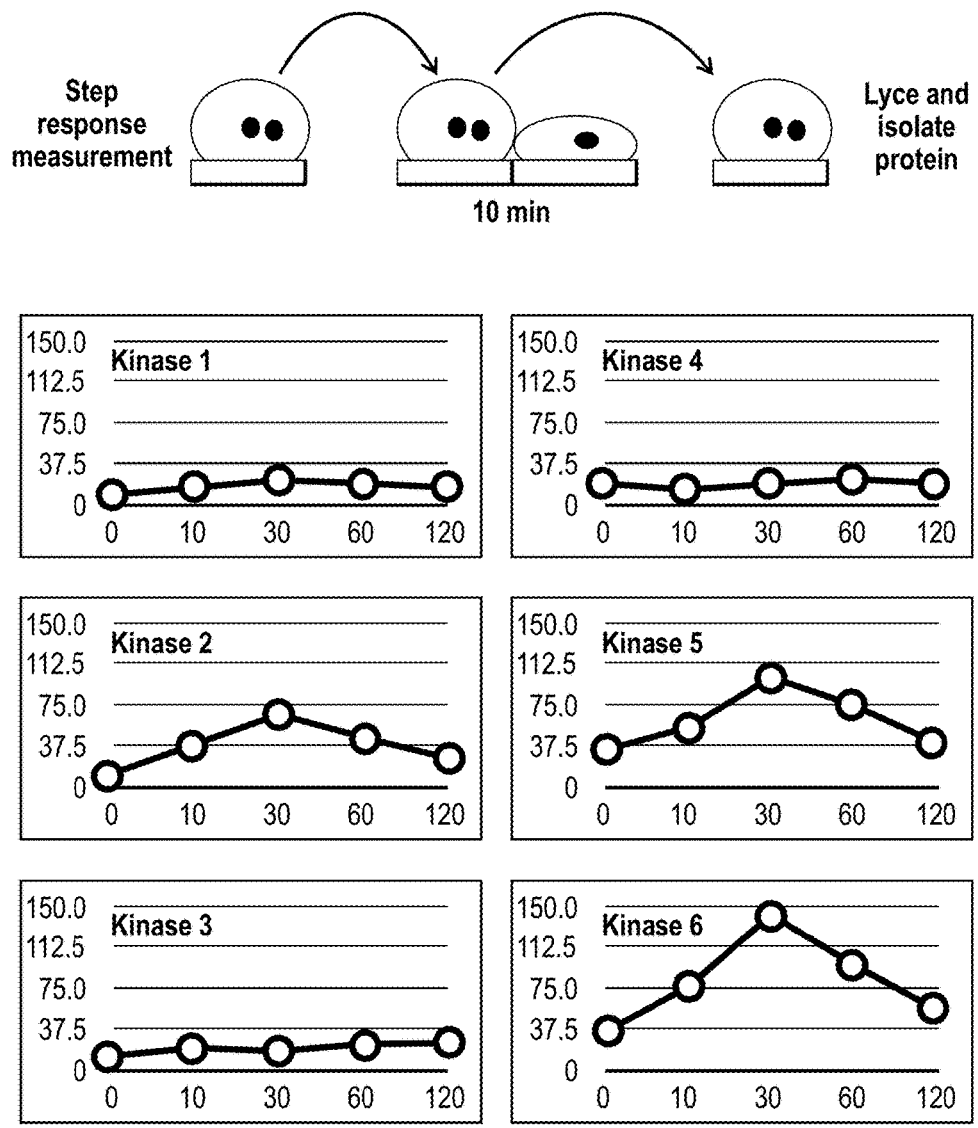
FIG. 14 depicts the dynamic responses of intracellular signaling kinases within hepatocytes during the first 120 minutes in response to the introduction of 3T3 cells in co-culture. By using the micromechanical substrates, hepatocytes are brought into contact with 3T3 fibroblasts for a short, defined period of time and then separated back to a pure hepatocyte population prior to cell lysis. The phosphorylation of various kinases was then measured using a cytometeric bead array.

For example, immunohistochemistry and Western blotting were used to characterize expression of the specific EC markers RECA, SE-1, PECAM and AcLDL in isolated primary rat LSECs were cultured under the following conditions: a) on the different ECM proteins including, Collagen-I, Fibronectin, Laminin, and Collagen-IV; b) with various combinations of supportive cells, using the micromechanical reconfigurable culture method described herein to enable tracking of individual cell types, separation into pure populations for analysis, and deconvolution of contact-mediated versus soluble signals; and c) in the presence of the tyrosine phosphatase inhibitor, orthovanadate (OV). Results of these studies are shown in FIGS. 9, 10 and 11.

Interestingly, using the methods described above, a decrease in the expression of SE-1 and increase expression of PECAM-1 was observed when LSEC were placed in culture; in addition, an effect of specific ECM components on the levels of expression of SE-1 was also observed, suggesting a role of ECM in modulating LSEC phenotype. Significantly, SE-1 expression could be maintained for longer periods through co-culture—up to 14 days in the optimal configuration involving co-cultivation with both hepatocytes and fibroblasts. The data also suggest that direct contact between LSECs and support cells is not necessary. To begin to gain a mechanistic insight into these observations, the role of tyrosine phosphorylation of cellular proteins in maintaining LSEC phenotype was investigated, since it has previously demonstrated that OV inhibited LSEC apoptosis (Fujimoto, H. et al. (2006) *Am J Pathol* 168, 1086-1096). It was found that SE-1 expression was strongly maintaining at day 3 when they were cultured in the presence of OV, suggesting that a decrease in protein phosphorylation is involved also in the loss of the phenotype. In addition, the co-culture of LSEC with hepatocytes or fibroblast-stabilized hepatocytes induced LSEC proliferation as well as the activation of the transcription factor STAT-1.

Collectively, the experiments described above led to the identification of novel microenvironmental regulators of the LSEC phenotype, which may be important for the development of better in vitro models the study of liver biology and tissue engineering constructs.

Selected Applications. In one embodiment, the inventive dynamic platform disclosed herein was used to study cell-cell interactions between hepatocytes and stromal cells in co-culture. As with many other cell types, interaction of epithelia with supportive stroma or 'feeder layers' promotes tissue-specific gene expression in vitro. In the case of primary hepatocytes, co-cultivation of hepatocytes with many different mesenchymal cell types (endothelia, fibroblasts, etc.) promotes retention of hepatocyte viability and liver-specific functions that are otherwise rapidly lost in vitro (Bhatia, S. N., Balis, U. J., Yarmush, M. L. & Toner, M. (1999) *Faseb J* 13, 1883-900). This robust 'co-culture' phenomena, though poorly understood, has wide-ranging applications in both therapeutic and diagnostic applications of engineered liver tissue (Tilles, A. W., Baskaran, H., Roy, P., Yarmush, M. L. & Toner, M. (2001) *Biotechnol Bioeng* 73, 379-89; Allen, J. W., Khetani, S. R. & Bhatia, S. N. (2005) *Toxicol Sci* 84, 110-9; and Guillouzo, A. (1998) *Environ Health Perspect* 106 Suppl 2, 511-32). Using both conventional techniques and micropatterning approaches, it has previously been found that the degree of interaction between the two cell types ('heterotypic interaction') modulated the amount of liver-specific function retained in vitro (Bhatia, S. N., Balis, U. J., Yarmush, M. L. & Toner, M. (1999) *Faseb J* 13, 1883-900; and Guguen-Guillouzo, C. & Guillouzo, A. (1983) *Mol Cell Biochem* 53-54, 35-56). These findings suggested an important role for proximity between the two cell types in the rescue of hepatocyte phenotype; however, the relative role of contact-mediated versus soluble signals, the dynamics of interaction, and the potential for reciprocal signaling had not been established.

Figure 3:
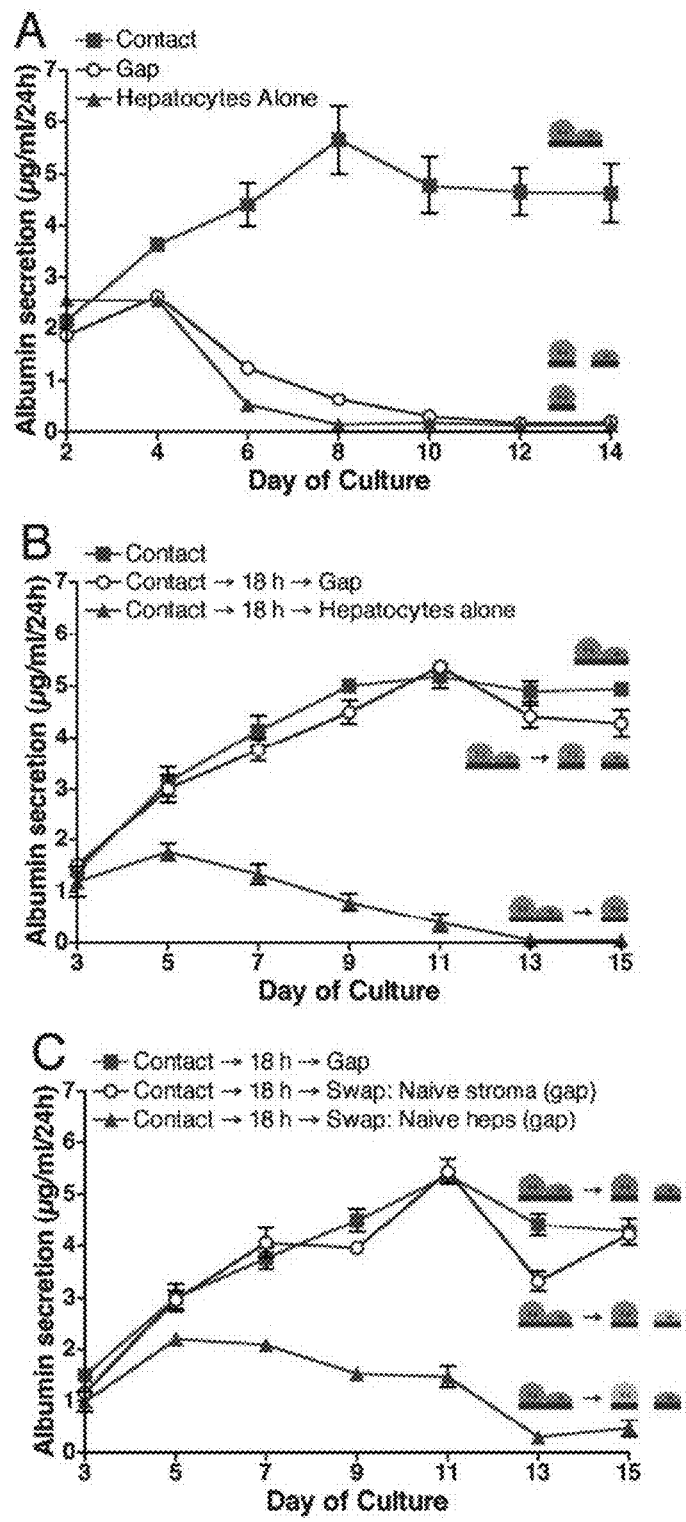
FIG. 3 depicts results of dynamic regulation of hepatocyte-stromal interactions, which reveals temporal dependencies in intercellular communication. (A) Contact between hepatocyte and fibroblast combs was required to maintain albumin secretion over a 2-wk period (red). In the gap mode (blue), function dropped almost as rapidly as with hepatocytes alone (green). (B) An 18-h period of transient initial contact followed by long-term culture in the gap mode (which allows diffusion of paracrine signals) resulted in sustained liver-specific function (blue) similar to that obtained with sustained contact (red). However, 18 h of initial contact followed by removal of adjacent stroma resulted in deterioration of function (green). (C) Following 18 h of initial contact, stroma were removed and replaced by nave stroma (in gap mode). Liver-specific function was maintained at similar levels (blue) to that obtained with no cell swapping (red). In a parallel experiment in which nave hepatocytes were substituted, liver-specific function was not maintained (green).

Hence, in order to explore this system using the µRC substrates, primary rat hepatocytes and Swiss 3T3 murine fibroblasts were cultured on opposing combs. Hepatocyte morphology and viability were assessed microscopically and albumin production was measured as a quantitative marker of liver-specific function. Comparison of cultures in the contact, gap, and separated modes demonstrated that contact was necessary for maintenance of liver-specific function (FIG. 3A). Even in the gap mode, which corresponded to only an 80-µm separation between the two cell populations, hepatocyte function declined at a rate similar to that of hepatocytes cultured alone. Next, dynamic experiments in which cells were repositioned following 18 h of contact were conducted. Here, transient contact alone proved insufficient to rescue the hepatocyte phenotype, and liver-specific functions rapidly declined. In contrast, transient contact followed by sustained culture in the gap mode provided complete rescue of liver-specific function (FIG. 3B). These observations thus imply a necessary role both for heterotypic contact and for soluble factors that diffuse across the gap.

Notably, it would appear that contact was required only initially, whereas soluble interactions were required for the duration of the experiment. This finding raised the possibility that reciprocal interactions—i.e., sustained alterations in fibroblast function as a result of hepatocyte contact—might play a role. In order to test this possibility, the 'modular' nature of the µRC platform was explored. Co-cultures were conducted in contact mode for 18 h as before; however, the fibroblasts were then replaced with naïve fibroblasts (no exposure to heterotypic contact) in gap mode. Under these conditions, paracrine signals provided by naïve fibroblasts were still sufficient to sustain hepatic functions (FIG. 3C). Conversely, if naïve hepatocytes were substituted, hepatic function deteriorated. Hence, the data are consistent with constitutive expression of critical soluble factors by fibroblasts independent of hepatocyte interaction rather than supporting a role for reciprocal cell-cell interaction.

Figure 4:
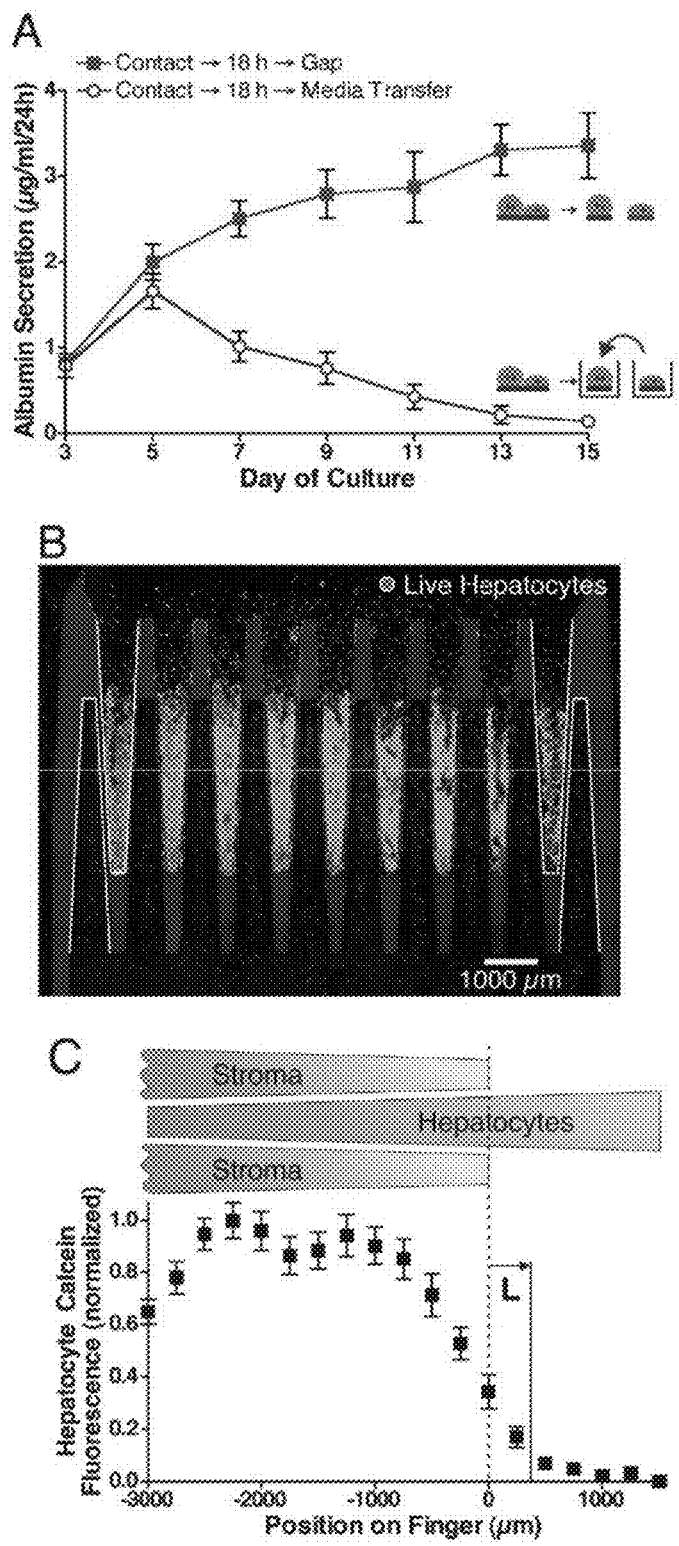
FIG. 4 depicts results which show the use of spatial reconfiguration to reveal short-range soluble signaling. (A) Following 18 h of initial contact, hepatocytes and stroma were separated into individual wells. Stromal conditioned media was transferred every 2 days to the hepatocytes, but liver-specific function declined (blue). In contrast, transient contact followed by microscale separation (using the gap mode) resulted in sustained function (red). (B) Loss in liverspecific function progresses to loss in hepatocyte viability. Hepatocyte viability was probed using a membrane integrity dye (calcein AM, green) with a nuclear counterstain for both cell types (blue). Following initial contact, cultures were maintained for two weeks in the gap mode, resulting in a sharp gradient in hepatocyte viability dependent on proximity to stroma (n>3, representative image shown). Selected comb fingers are outlined in white for clarity. (C) Quantified calcein fluorescence along the length of a comb finger (n=9). L, the characteristic decay length of viability, is measured to be 325 μm using an exponential fit over x>0.

To investigate the importance of cell proximity, device pairs were separated into separate wells following 18 h of initial contact. Conditioned media was then transferred from the fibroblast well to the hepatocyte well every two days. However, hepatic function was not maintained (FIG. 4A), underscoring the importance of close positioning in the gap configuration. Further, microscopic examination of co-cultures yielded a striking observation: in cultures stabilized via transient contact followed by gap mode, hepatocytes towards the rear of each comb finger lost viability over the course of two weeks (FIG. 4B). Hepatocyte-fibroblast distance is greater in this region compared to the rest of the comb finger due to the geometry of the device in the gap configuration (FIG. 1A, inset). Quantifying viability using a fluorescent membrane integrity dye yielded a characteristic length of decay in viability of approximately 325 µm (FIG. 4C). It was demonstrated through finite element modeling that diffusion of a rapidly decaying (on the order of hours) or rapidly consumed (comparable to rate of production) soluble factor could produce concentration profiles similar to the survival pattern of FIG. 4B (FEM Diffusion Model). These data suggest that the fibroblast-derived soluble signals critical for rescue of the hepatocyte phenotype and viability are effective over a very limited range, on the order of only 10 cell diameters.

Figure 5:
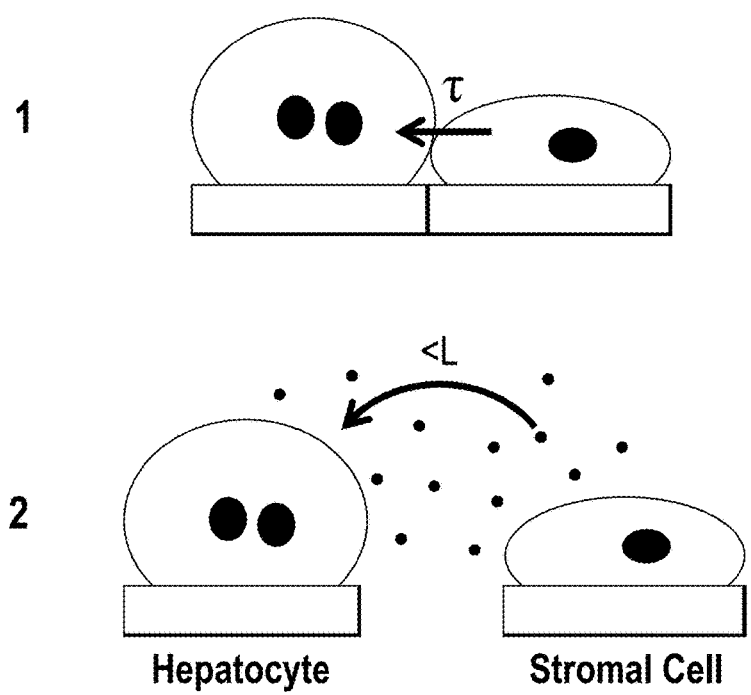
FIG. 5 depicts one proposed model for intercellular communication. Maintenance of liver-specific function in hepatocytes requires (1) an initial short-term (τ is about 18 h) contact-mediated signal from stromal cells, followed by (2) sustained short-range (L is about 325 μm) soluble signaling from the stroma.

Preservation of hepatocyte viability and liver-specific functions in co-culture appears to depend on an initial contact-mediated signal followed by a sustained short-range soluble signal from fibroblasts to hepatocytes (FIG. 5). It is not clear whether the contact-mediated signal is junctional in nature (hepatocytes and 3T3 fibroblasts do not express similar cadherin or connexin subtypes) or due to cell-associated matrix molecules. It is also unknown why only transient contact is required. One possibility is that transient contact triggers an irreversible signaling pathway. Alternatively, the contaminating cells that remain after separation (FIG. 2C) may play a role in the response. This seems unlikely since hepatic function could not be maintained in gap mode without initial contact, even when low numbers of fibroblasts were doped onto the hepatocyte fingers (data not shown). A third possibility is that fibroblasts secrete critical extracellular matrix components onto the hepatocyte fingers during the transient contact period that help to sustain function thereafter. Regardless, these data point to the possibility that hepatocytes could be preconditioned and subsequently sustained without supportive stromal cells, a finding with significant practical implications for the therapeutic and diagnostic applications of hepatocytes. Notably, only the peripheral hepatocytes can directly contact fibroblasts, yet the entire population is affected. This finding is consistent with previous reports but the precise mechanism has not yet been established Finally, the possible reasons that soluble signals are effective over very limited distances include: that the critical factors are highly labile, are active at relatively high local concentration, or are rapidly sequestered extracellularly via binding to extracellular matrix proteins.

As the example above suggests, µRC may be utilized to execute a number of previously inaccessible experiments. The disclosure herein establishes that it is possible to decouple contact-mediated and soluble signals, dynamically modulate both contact-mediated and soluble cell-cell signaling, examine the reversibility of a pathway upon removal of the triggering signal, test for the presence of reciprocal cell-cell signaling, and measure the effective range of soluble signals. In other words, the disclosure herein establishes that micromechanical culture substrates are a robust and generalizable tool. Since, in certain embodiments, the device surface is comparable to tissue culture plastic, it should be readily adapted to a variety of cell types and molecular techniques.

Figure 6:
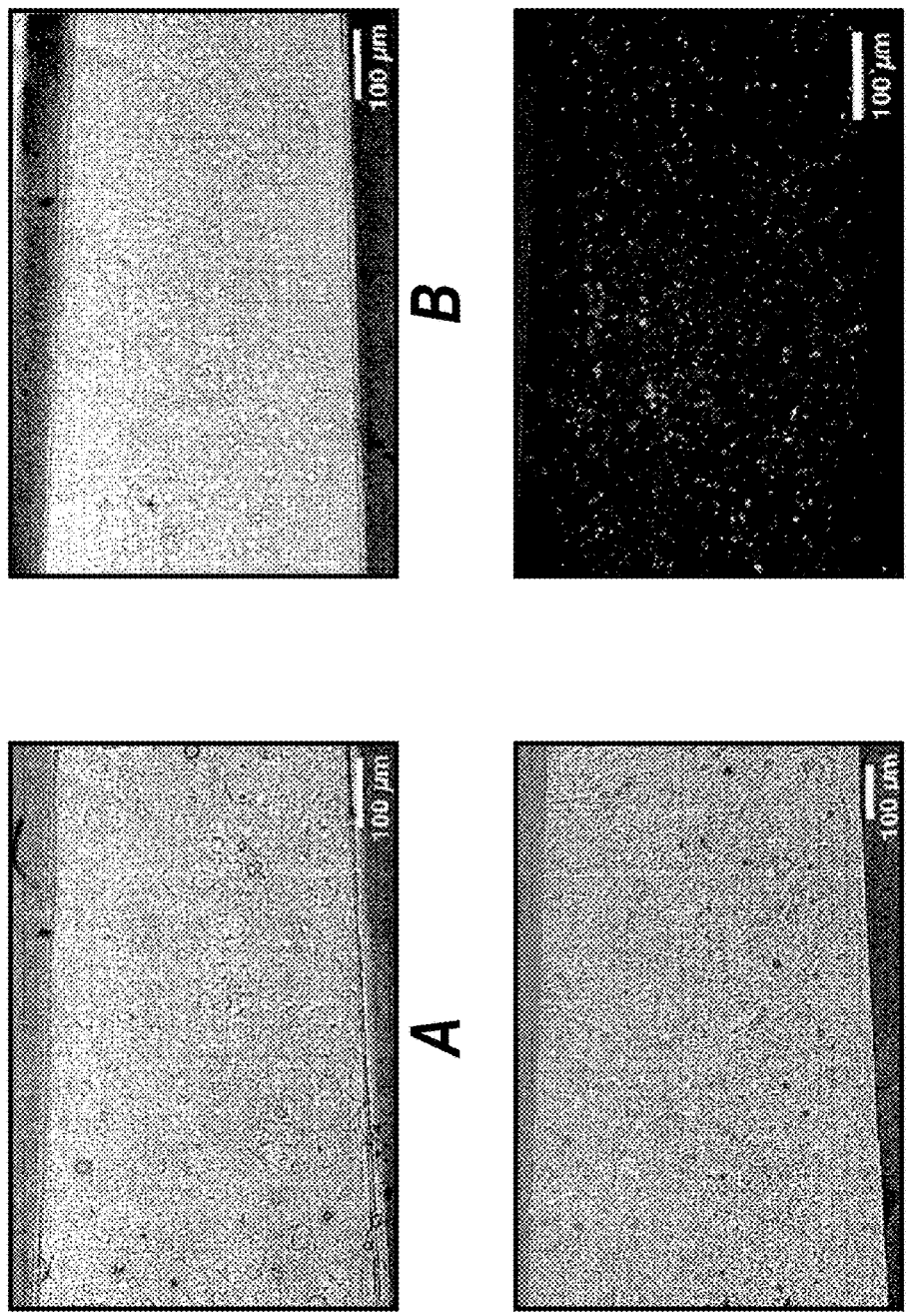
FIG. 6 depicts results demonstrating that micromechanical substrates can be generalized to other cell types and biological techniques. (A) Bipotential mouse embryonic liver progenitor cells cultured for 1 day on a micromechanical substrate. The BMEL cell line, 9A1, was provided by Dr. Mary Weiss (Institut Pasteur) and cultured as described previously (Strick-Marchand, H., Morosan, S., Charneau, P., Kremsdorf, D. & Weiss, M. C. (2004) *Proc Natl Acad Sci USA* 101, 8360-5; and Strick-Marchand, H. & Weiss, M. C. (2002) *Hepatology* 36, 794-804). In brief, cells were cultured on collagen in RPMI 1640 medium with glutamax (Invitrogen, Carlsbad, Calif.), containing 30 ng/mL human IGF-II (Peprotech, Rocky Hill, N.J.), 50 ng/mL human EGF (Peprotech), and 10 mg/mL recombinant human insulin (Invitrogen). (B) Primary rat liver sinusoidal endothelial cells (LSEC) cultured for 1 day on a collagen-coated micromechanical substrate. Briefly, LSEC were isolated from the nonparenchymal fraction of the liver through a 25%/50% Percoll gradient (Zhang, B., Borderie, D., Sogni, P., Soubrane, O., Houssin, D. & Calmus, Y. (1997) *J Hepatol* 26, 1348-55) and cultured in the presence of VEGF (R&D Systems, Minneapolis, Minn.). (C) OP9 bone marrow stromal cells (ATCC, Manassas, Va.) cultured for 1 day on a collagen-coated micromechanical substrate, using alpha minimum essential medium without ribonucleosides and deoxyribonucleosides with 2 mM L-glutamine and 1.5 g/L sodium bicarbonate, 80%; fetal bovine serum, 20% (all from Invitrogen). (D) Cells can be transfected with siRNA while adhered to micromechanical substrates, allowing selective delivery using the separated mode. Fluorescent image of Swiss 3T3 fibroblasts transfected with siRNA sequence (against Lamin A) with FITC fluorophore conjugated to 5' end of sense strand (Dharmacon, Lafayette, Colo.). Transfection was performed using Lipofectamine 2000 (Invitrogen) on cells adhered to the substrate.

For example, compatibility with liver progenitors, sinusoidal endothelial cells, and bone marrow stromal cells, as well as transfection of siRNA into individual cell populations has been demonstrated (FIG. 6). This methodology will find utility in the investigation of cellular niches (Moore, K. A. & Lemischka, I. R. (2006) *Science* 311, 1880-1885), in the dissection of developmental processes (Lemaigre, F. & Zaret, K. S. (2004) *Curr Opin Genet Dev* 14, 582-90), and in the study of disease progression—in particular in tissues where stromal interactions are thought to play a role (e.g., tumorigenesis; Zigrino, P., Loffek, S. & Mauch, C. (2005) *Biochimie* 87, 321-328).

Selected Methods of the Invention. The following methods illustrate different aspects and embodiments of the present invention, and are not intended to limit the scope of the invention.

One aspect of the invention relates to a method comprising the steps of culturing at least one cell of a first type on a first component; culturing at least one cell of a second type on a second component; and placing the first component at a distance from or in contact with the second component for a time; thereby co-culturing the at least one cell of a first type and the at least one cell of a second type.

As discussed above, cell-cell interactions play a critical role in driving cell differentiation during development. The reconfigurable substrates of the invention could be used to simulate these processes in vitro. For example, stem cells or progenitor cells can be driven down a specific differentiation pathway by bringing them into contact with a series of different cell types. Therefore, one aspect of the invention relates to a method of stimulating cell differentiation comprising the steps of:

culturing a plurality of cells of a first type on a first component, wherein the cells of a first type are stem cells or progenitor cells;

culturing a plurality of cells of a second type on a second component, wherein the cells of a second type secrete a differentiation-inducing signal; and placing the first component at a distance from or in contact with the second component for a time.

In certain embodiments, the present invention relates to the aforementioned method and any of the attendant limitations, further comprising the step of determining if the cells of a first type have differentiated.

In certain embodiments, the present invention relates to the aforementioned method and any of the attendant limitations, wherein the cells of a first type are mammalian cells.

In certain embodiments, the present invention relates to the aforementioned method and any of the attendant limitations, wherein the cells of a first type are human cells.

In certain embodiments, the present invention relates to the aforementioned method and any of the attendant limitations, wherein the cells of a first type are early embryonic stem cells, blastocyst embryonic stem cells, fetal stem cells, umbilical cord stem cells, or adult stem cells.

In certain embodiments, the present invention relates to the aforementioned method and any of the attendant limitations, wherein the cells of a first type are adult stem cells isolated from nerve cells, blood cells, muscle cells, skin cells, or bone cells.

In certain embodiments, the present invention relates to the aforementioned method and any of the attendant limitations, wherein the cells of a first type are human embryonic stem cells.

In certain embodiments, the present invention relates to the aforementioned method and any of the attendant limitations, wherein the cells of a second type are mammalian cells.

In certain embodiments, the present invention relates to the aforementioned method and any of the attendant limitations, wherein the cells of a second type are human cells.

In certain embodiments, the present invention relates to the aforementioned methods and any of the attendant limitations, wherein the cells of a second type secrete morphogens.

In certain embodiments, the present invention relates to the aforementioned methods and any of the attendant limitations, wherein the cells of a second type secrete morphogens selected from the group consisting of decapentaplegic/transforming growth factor beta, hedgehog/sonic hedgehog, wingless/wnt, epidermal growth factor, and fibroblast growth factor.

In certain embodiments, the present invention relates to the aforementioned methods and any of the attendant limitations, wherein the cells of a second type secrete morphogens selected from the group consisting of human OP-1, mouse OP-1, human OP-2, mouse OP-2, 60A, GDF-1, BMP2A, BMP2B, DPP, Vgl, Vgr-1, BMP3, BMP5, and BMP6.

Further, the effects of soluble factors on any cell type, not just stem-cells, may be studied using the devices of the invention. Therefore, another aspect of the invention relates to a method of exposing cells to cytokines comprising the steps of:

culturing a plurality of cells of a first type on a first component, wherein the cells of a first type are target cells comprising a receptor;

culturing a plurality of cells of a second type on a second component, wherein the cells of a second type secrete soluble signal; and placing the first component at a distance from or in contact with the second component for a time.

In certain embodiments, the present invention relates to the aforementioned methods and any of the attendant limitations, further comprising the step of determining the effect of soluble signal exposure on the cells of a first type.

In certain embodiments, the present invention relates to the aforementioned method and any of the attendant limitations, wherein the cells of a first type are mammalian cells.

In certain embodiments, the present invention relates to the aforementioned method and any of the attendant limitations, wherein the cells of a first type are human cells.

In certain embodiments, the present invention relates to the aforementioned methods and any of the attendant limitations, wherein the cells of a first type comprise receptors for a member of the VEGF family, VEGF-D, a member of the MIP family, MIP-1γ, ceruloplasmin, nitric oxide, gases, or growth factors.

In certain embodiments, the present invention relates to the aforementioned methods and any of the attendant limitations, wherein the cells of a first type comprise DLK, Dlk-1, a cahedrins, or T-cahedrin.

In certain embodiments, the present invention relates to the aforementioned method and any of the attendant limitations, wherein the cells of a second type are mammalian cells.

In certain embodiments, the present invention relates to the aforementioned method and any of the attendant limitations, wherein the cells of a second type are human cells.

In certain embodiments, the present invention relates to the aforementioned methods and any of the attendant limitations, wherein the cells of a second type secrete hematopoietins, interferons, tumor necrosis factors, chemokines, or a combination thereof.

In certain embodiments, the present invention relates to the aforementioned methods and any of the attendant limitations, wherein the cells of a second type secrete a member of the VEGF family, VEGF-D, a member of the MIP family, MIP-1γ, ceruloplasmin, nitric oxide, gases, or growth factors In particular, the inductive effect of cytokine gradients can be studied by varying the separation between inducer and target cell populations. Therefore, another aspect of the invention relates to a method of exposing cells to cytokines comprising the steps of:

culturing a plurality of cells of a first type on a first component, wherein the cells of a first type are target cells comprising a cytokine receptor;

culturing a plurality of cells of a second type on a second component, wherein the cells of a second type secrete a cytokine; and placing the first component at a distance from or in contact with the second component for a time.

In certain embodiments, the present invention relates to the aforementioned methods and any of the attendant limitations, further comprising the step of determining the effect of cytokine exposure on the cells of a first type.

In certain embodiments, the present invention relates to the aforementioned method and any of the attendant limitations, wherein the cells of a first type are mammalian cells.

In certain embodiments, the present invention relates to the aforementioned method and any of the attendant limitations, wherein the cells of a first type are human cells.

In certain embodiments, the present invention relates to the aforementioned methods and any of the attendant limitations, wherein the cells of a first type comprise cytokine receptors selected from the group consisting of hematopoietin family receptors, interferon family receptors, tumor necrosis factor family receptors, and chemokine family receptors.

In certain embodiments, the present invention relates to the aforementioned methods and any of the attendant limitations, wherein the cells of a first type comprise cytokine receptors selected from the group consisting of receptors for IL-1α, IL-1β, IL-2, IL-3, IL-4, IL-5, IL-6, IL-7, IL-8, IL-9, IL-12, IL-15, GM-CSF, IFN-α, IFN-β, IFN-γ, TNF-α, TNF-β, CD40, Fas, MIP-1α, MIP-1β, RANTES, CCR5, and CXCR4.

In certain embodiments, the present invention relates to the aforementioned method and any of the attendant limitations, wherein the cells of a second type are mammalian cells.

In certain embodiments, the present invention relates to the aforementioned method and any of the attendant limitations, wherein the cells of a second type are human cells.

In certain embodiments, the present invention relates to the aforementioned methods and any of the attendant limitations, wherein the cells of a second type secrete hematopoietins, interferons, tumor necrosis factors, chemokines, or a combination thereof.

In certain embodiments, the present invention relates to the aforementioned methods and any of the attendant limitations, wherein the cells of a second type secrete IL-1α, IL-1β, IL-2, IL-3, IL-4, IL-5, IL-6, IL-7, IL-8, IL-9, IL-12, IL-15, GM-CSF, IFN-α, IFN-β, IFN-γ, TNF-α, TNF-β, CD40, Fas, MIP-1α, MIP-1β, RANTES, CCR5, or CXCR4.

Interactions between a tumor and its surrounding stroma are known to play an important role in determining the progression of certain types of cancer; reconfigurable substrates may be used to study these interactions. For example, tumor cells can be switched from co-cultivation with normal fibroblasts to cancer-associated fibroblasts using reconfigurable substrates. Dynamic changes in the biology of the tumor cells can then be measured. It follows therefore that one aspect of the invention relates to a method of exposing tumor cells to non-tumor cells comprising the steps of:

culturing a plurality of cells of a first type on a first component, wherein the cells of a first type are tumor cells;

culturing a plurality of cells of a second type on a second component; and placing the first component at a distance from or in contact with the second component for a time.

In certain embodiments, the present invention relates to the aforementioned method and any of the attendant limitations, further comprising the step of determining changes in biology of the cells of a first type.

In certain embodiments, the present invention relates to the aforementioned method and any of the attendant limitations, wherein the cells of a first type are mammalian cells.

In certain embodiments, the present invention relates to the aforementioned method and any of the attendant limitations, wherein the cells of a first type are human cells.

In certain embodiments, the present invention relates to the aforementioned methods and any of the attendant limitations, wherein the cells of a first type are selected from the group consisting of tumor cells of the anus, bladder, bile duct, bone, brain, breast, cervix, colon/rectum, duodenum, endometrium, esophagus, eye, gallbladder, head, neck, liver, larynx, lung, mouth, pancreas, penis, prostate, kidney, ovaries, skin, stomach, testicles, and thyroid.

In certain embodiments, the present invention relates to the aforementioned methods and any of the attendant limitations, wherein the cells of a first type are tumor cells selected from the group consisting of carcinoma, lymphomas, leukemias, sarcomas, mesotheliomas, gliomas, germinomas, and choriocarcinomas.

In certain embodiments, the present invention relates to the aforementioned method and any of the attendant limitations, wherein the cells of a second type are mammalian cells.

In certain embodiments, the present invention relates to the aforementioned method and any of the attendant limitations, wherein the cells of a second type are human cells.

In certain embodiments, the present invention relates to the aforementioned method and any of the attendant limitations, wherein the cells of a second type are selected from the group consisting of cells of the anus, bladder, bile duct, bone, brain, breast, cervix, colon/rectum, duodenum, endometrium, esophagus, eye, gallbladder, head, neck, liver, larynx, lung, mouth, pancreas, penis, prostate, kidney, ovaries, skin, stomach, testicles, and thyroid.

In certain embodiments, the present invention relates to the aforementioned method and any of the attendant limitations, wherein the cells of a second type are cancer-associated cells.

In certain embodiments, the present invention relates to the aforementioned method and any of the attendant limitations, wherein the cells of a second type are fibroblasts.

In certain embodiments, the devices of the invention can be used for drug discovery and toxicity testing. For example, the reconfigurable substrates could be used to isolate specific secreted soluble factors, for example a factor secreted by one cell type and which has a protective or regenerative effect on another cell type. The reconfigurable substrate would be utilized to bring different cell types close together to allow soluble interaction while preventing contact interaction. RNAi techniques would then used to knockdown expression of specific soluble factors in order to isolate the critical molecules. This method is suitable for models including but not limited to liver hepatocytes co-cultivated with nonparenchymal support cells. Specifically, another aspect of the invention relates to a method of isolating a soluble factor comprising the steps of:

culturing a plurality of cells of a first type on a first component;

culturing a plurality of cells of a second type on a second component, wherein the cells of a second type secrete a soluble factor; and placing the first component at a distance from but not in contact with the second component for a time.

In certain embodiments, the present invention relates to the aforementioned method and any of the attendant limitations, further comprising the step of using RNAi techniques to knockdown expression of the soluble factor.

In certain embodiments, the present invention relates to the aforementioned method and any of the attendant limitations, further comprising the step of determining the effect of the soluble factor on the cells of a first type.

In certain embodiments, the present invention relates to the aforementioned method and any of the attendant limitations, wherein the soluble factor has a protective or regenerative effect on the cells of a first type.

In certain embodiments, the present invention relates to the aforementioned method and any of the attendant limitations, wherein the soluble factor is selected from the group consisting of BDNF, CNTF, Dvl-1, EGF, Endostatin, FGF, GDNF, GM-CSF, Heregulin, IGF, IL, Insulin, Interferon, Jagged1, M-CSF, NAG-1, NGF, NT, PDGF, PEDF, Prolactin, SDF, SF-1, TGF, TNF, VEGF, and Wnt.

In certain embodiments, the present invention relates to the aforementioned method and any of the attendant limitations, wherein the soluble factor is selected from the group consisting of fibrinogen, laminin, collagen IV, tenascin, fibronectin, collagen, bovine pituitary extract, EGF, hepatocyte growth factor, keratinocyte growth factor, hydrocortisone, dimethyl sulphoxide, recombinant human epidermal growth factor, insulin, sodium selenite, transferrin, hydrocortisone, basic fibroblast growth factor, and leukemia inhibitory factor.

In certain embodiments, the present invention relates to the aforementioned method and any of the attendant limitations, wherein the cells of a first type are mammalian cells.

In certain embodiments, the present invention relates to the aforementioned method and any of the attendant limitations, wherein the cells of a first type are human cells.

In certain embodiments, the present invention relates to the aforementioned method and any of the attendant limitations, wherein the cells of a first type are selected from the group consisting of cells of the anus, bladder, bile duct, bone, brain, breast, cervix, colon/rectum, duodenum, endometrium, esophagus, eye, gallbladder, head, neck, liver, larynx, lung, mouth, pancreas, penis, prostate, kidney, ovaries, skin, stomach, testicles, and thyroid.

In certain embodiments, the present invention relates to the aforementioned method and any of the attendant limitations, wherein the cells of a second type are mammalian cells.

In certain embodiments, the present invention relates to the aforementioned method and any of the attendant limitations, wherein the cells of a second type are human cells.

In certain embodiments, the present invention relates to the aforementioned method and any of the attendant limitations, wherein the cells of a second type are selected from the group consisting of cells of the anus, bladder, bile duct, bone, brain, breast, cervix, colon/rectum, duodenum, endometrium, esophagus, eye, gallbladder, head, neck, liver, larynx, lung, mouth, pancreas, penis, prostate, kidney, ovaries, skin, stomach, testicles, and thyroid.

The reconfigurable substrates if the invention could be used in organ models (including but not limited to the liver) for the screening of toxic compounds. Because cells in mixed culture can be temporarily separated into individual culture wells, compound exposure can be limited to a specific subpopulation of cells in a mixed culture model, reducing off-target effects. Also, culturing parenchymal and nonparenchymal cells in the gap configuration may yield more physiological models—cell contact is abrogated while short-range soluble interactions are preserved, which can better mimic certain in vivo physiologies.

The use of reconfigurable substrates could also be used to separate cells in mixed culture into pure populations, to facilitate clean measurements of cell behavior, whether at the RNA, protein, or organelle activity level. This would be useful, for example, in detecting toxic responses in which the metabolite of one cell population is toxic to a second cell population. Remarkably, use of reconfigurable substrates simultaneously allows both intimate cell-cell interactions (for example via short-range soluble signaling) and the ability to separate into pure populations.

It follows that one aspect of the invention relates to a method of selectively exposing a subpopulation of cells from a mixed culture of cells to a compound comprising the steps of:

culturing a mixed culture of cells comprising a plurality of cells of a first type and a plurality of cells of a second type; wherein the cells of a first type are cultured on a first component, the cells of a second type are cultured on a second component, and the first component is at a distance from or in contact with the second component;

separating the first component from the second component;

exposing the cells of a first type on the first component to a compound for a time; and placing the first component in proximity to or in contact with the second component.

In certain embodiments, the present invention relates to the aforementioned method and any of the attendant limitations, wherein the compound is a toxic compound, exposure to which results in the death of at least some of the cells of a first type.

In certain embodiments, the present invention relates to the aforementioned method and any of the attendant limitations, wherein the cells of a first type are mammalian cells.

In certain embodiments, the present invention relates to the aforementioned method and any of the attendant limitations, wherein the cells of a first type are human cells.

In certain embodiments, the present invention relates to the aforementioned method and any of the attendant limitations, wherein the cells of a first type are selected from the group consisting of cells of the anus, bladder, bile duct, bone, brain, breast, cervix, colon/rectum, duodenum, endometrium, esophagus, eye, gallbladder, head, neck, liver, larynx, lung, mouth, pancreas, penis, prostate, kidney, ovaries, skin, stomach, testicles, and thyroid.

In certain embodiments, the present invention relates to the aforementioned method and any of the attendant limitations, wherein the cells of a second type are mammalian cells.

In certain embodiments, the present invention relates to the aforementioned method and any of the attendant limitations, wherein the cells of a second type are human cells.

In certain embodiments, the present invention relates to the aforementioned method and any of the attendant limitations, wherein the cells of a second type are selected from the group consisting of cells of the anus, bladder, bile duct, bone, brain, breast, cervix, colon/rectum, duodenum, endometrium, esophagus, eye, gallbladder, head, neck, liver, larynx, lung, mouth, pancreas, penis, prostate, kidney, ovaries, skin, stomach, testicles, and thyroid.

In another embodiment, reconfigurable substrates to create liver models that support infection of a hepatitis virus. It has been reported that co-cultivated liver endothelial cells cause liver hepatocytes to be more susceptible to infection by Hepatitis C. The reconfigurable substrates of the invention could be used to create a co-culture or tri-culture system where endothelial cells maintain and influence hepatocytes separated using the gap configuration. Such a system would mimic in vivo physiology, in which sinusoidal endothelial cells are near hepatocytes but separated by the space of Disse. Also, since hepatocytes are maintained in a pure monolayer on their individual comb fingers, evaluation by microscopy or by RNA, protein, or organelle activity level would be facilitated. In addition, configurable substrates could be used to identify specific molecules that influence hepatitis infectivity. For example, soluble factors from endothelial cells that modulate hepatocyte susceptibility to hepatitis viruses could be identified using aforementioned methods, such as siRNA knockdown.

In other words, another aspect of the invention relates to a method of selectively exposing a mixed culture of cells to a compound comprising the steps of:

culturing a mixed culture of cells comprising a plurality of cells of a first type and a plurality of cells of a second type; wherein the cells of a first type are cultured on a first component, the cells of a second type are cultured on a second component, and the first component is at a distance from or in contact with the second component; and exposing the cells of a first type on the first component and the cells of a second type on a second component to a compound for a time.

In certain embodiments, the present invention relates to the aforementioned method and any of the attendant limitations, wherein the compound is a toxic compound, exposure to which results in the death of at least some of the cells of a first type, some of the cells of a second type, or cells of both types.

In certain embodiments, the present invention relates to the aforementioned method and any of the attendant limitations, wherein the cells of a first type are mammalian cells.

In certain embodiments, the present invention relates to the aforementioned method and any of the attendant limitations, wherein the cells of a first type are human cells.

In certain embodiments, the present invention relates to the aforementioned method and any of the attendant limitations, wherein the cells of a first type are selected from the group consisting of cells of the anus, bladder, bile duct, bone, brain, breast, cervix, colon/rectum, duodenum, endometrium, esophagus, eye, gallbladder, head, neck, liver, larynx, lung, mouth, pancreas, penis, prostate, kidney, ovaries, skin, stomach, testicles, and thyroid.

In certain embodiments, the present invention relates to the aforementioned method and any of the attendant limitations, wherein the cells of a second type are mammalian cells.

In certain embodiments, the present invention relates to the aforementioned method and any of the attendant limitations, wherein the cells of a second type are human cells.

In certain embodiments, the present invention relates to the aforementioned method and any of the attendant limitations, wherein the cells of a second type are selected from the group consisting of cells of the anus, bladder, bile duct, bone, brain, breast, cervix, colon/rectum, duodenum, endometrium, esophagus, eye, gallbladder, head, neck, liver, larynx, lung, mouth, pancreas, penis, prostate, kidney, ovaries, skin, stomach, testicles, and thyroid.

In another embodiment, in addition to the selective stimulation described above, one can separate a subpopulation of cells from a culture in order to assay those cells specifically; this is known as selective interrogation. One example of selective interrogation is shown in FIG. 11, where SEC cells are separated out from a culture of many cell types, and a Western Blot is performed on the purified SEC population. Another example is in FIG. 15, where hepatocytes and 3T3 fibroblasts are separated before viability assays are performed on each population.

It follows that one aspect of the invention relates to a method of selectively assaying a subpopulation of cells from a mixed culture of cells comprising the steps of:

culturing a mixed culture of cells comprising a plurality of cells of a first type and a plurality of cells of a second type; wherein the cells of a first type are cultured on a first component, the cells of a second type are cultured on a second component, and the first component is at a distance from or in contact with the second component;

separating the first component from the second component; and assaying the cells of a first type, the cells of the second type, or both.

In certain embodiments, the present invention relates to the aforementioned method and any of the attendant limitations, wherein the assay is a viability assay.

In certain embodiments, the present invention relates to the aforementioned method and any of the attendant limitations, wherein the cells of a first type are mammalian cells.

In certain embodiments, the present invention relates to the aforementioned method and any of the attendant limitations, wherein the cells of a first type are human cells.

In certain embodiments, the present invention relates to the aforementioned method and any of the attendant limitations, wherein the cells of a first type are selected from the group consisting of cells of the anus, bladder, bile duct, bone, brain, breast, cervix, colon/rectum, duodenum, endometrium, esophagus, eye, gallbladder, head, neck, liver, larynx, lung, mouth, pancreas, penis, prostate, kidney, ovaries, skin, stomach, testicles, and thyroid.

In certain embodiments, the present invention relates to the aforementioned method and any of the attendant limitations, wherein the cells of a second type are mammalian cells.

In certain embodiments, the present invention relates to the aforementioned method and any of the attendant limitations, wherein the cells of a second type are human cells.

In certain embodiments, the present invention relates to the aforementioned method and any of the attendant limitations, wherein the cells of a second type are selected from the group consisting of cells of the anus, bladder, bile duct, bone, brain, breast, cervix, colon/rectum, duodenum, endometrium, esophagus, eye, gallbladder, head, neck, liver, larynx, lung, mouth, pancreas, penis, prostate, kidney, ovaries, skin, stomach, testicles, and thyroid.

For all of the methods described herein, a variety of different reconfigurable substrates can be used, for a variety of times, in a variety of configurations. For example, In certain embodiments, the present invention relates to any of the aforementioned methods and any of the attendant limitations, wherein the distance is in the range of about 1 μm to about 1,000 μm.

In certain embodiments, the present invention relates to any of the aforementioned methods and any of the attendant limitations, wherein the distance is in the range of about 10 μm to about 200 μm.

In certain embodiments, the present invention relates to any of the aforementioned methods and any of the attendant limitations, wherein the distance is in the range of about 50 μm to about 100 μm.

As used herein, fingers should be understood to be protrusions like the teeth of a comb. See FIG. 1e for an example.

In certain embodiments, the present invention relates to any of the aforementioned methods and any of the attendant limitations, wherein the first component comprises a first plurality of fingers.

In certain embodiments, the present invention relates to any of the aforementioned methods and any of the attendant limitations, wherein each finger in the first plurality of fingers is tapered.

In certain embodiments, the present invention relates to any of the aforementioned methods and any of the attendant limitations, wherein the ratio of the lengths of the ends of each finger in the first plurality of fingers is about 3:1.

In certain embodiments, the present invention relates to any of the aforementioned methods and any of the attendant limitations, wherein the second component comprises second a plurality of fingers.

In certain embodiments, the present invention relates to any of the aforementioned methods and any of the attendant limitations, wherein each finger in the second plurality of fingers is tapered.

In certain embodiments, the present invention relates to any of the aforementioned methods and any of the attendant limitations, wherein the ratio of the lengths of the ends of each finger in the second plurality of fingers is about 3:1.

In certain embodiments, the present invention relates to any of the aforementioned methods and any of the attendant limitations, wherein the length of each finger in the first plurality of fingers is about 1 mm to about 50 mm.

In certain embodiments, the present invention relates to any of the aforementioned methods and any of the attendant limitations, wherein the length of each finger in the first plurality of fingers is about 1 mm to about 1 mm.

In certain embodiments, the present invention relates to any of the aforementioned methods and any of the attendant limitations, wherein the length of each finger in the first plurality of fingers is about 5 mm.

In certain embodiments, the present invention relates to any of the aforementioned methods and any of the attendant limitations, wherein the length of each finger in the second plurality of fingers is about 1 mm to 50 mm.

In certain embodiments, the present invention relates to any of the aforementioned methods and any of the attendant limitations, wherein the length of each finger in the second plurality of fingers is about 1 mm to about 10 mm.

In certain embodiments, the present invention relates to any of the aforementioned methods and any of the attendant limitations, wherein the length of each finger in the second plurality of fingers is about 5 mm.

In certain embodiments, the present invention relates to any of the aforementioned methods and any of the attendant limitations, wherein the first plurality of fingers and the second plurality of fingers are structured and arranged to interdigitate with one another in a substantially coplanar fashion.

As used herein latch is a type of mechanical hardware, specifically a flexure, that is used to join two (or more) objects or surfaces together while allowing for the regular or eventual separation of the objects or surfaces. See, for example, the snap-lock arm in FIG. 1e.

In certain embodiments, the present invention relates to any of the aforementioned methods and any of the attendant limitations, wherein the first component comprises at least or exactly two latches, and the latches are on opposite sides of the first component.

In certain embodiments, the present invention relates to any of the aforementioned methods and any of the attendant limitations, wherein the second component comprises at least or exactly two latches, and the latches are on opposite sides of the second component.

In certain embodiments, the present invention relates to any of the aforementioned methods and any of the attendant limitations, wherein the first component comprises at least or exactly two slots, and the slots are on opposite sides of the first component.

In certain embodiments, the present invention relates to any of the aforementioned methods and any of the attendant limitations, wherein the first component comprises at least or exactly four slots, and the slots are on opposite sides of the first component.

In certain embodiments, the present invention relates to any of the aforementioned methods and any of the attendant limitations, wherein the first component comprises at least or exactly six slots, and the slots are on opposite sides of the first component.

In certain embodiments, the present invention relates to any of the aforementioned methods and any of the attendant limitations, wherein the second component comprises at least or exactly two slots, and the slots are on opposite sides of the second component.

In certain embodiments, the present invention relates to any of the aforementioned methods and any of the attendant limitations, wherein the second component comprises at least or exactly four slots, and the slots are on opposite sides of the second component.

In certain embodiments, the present invention relates to any of the aforementioned methods and any of the attendant limitations, wherein the second component comprises at least or exactly six slots, and the slots are on opposite sides of the second component.

In certain embodiments, the present invention relates to any of the aforementioned methods and any of the attendant limitations, wherein the slots are V-shaped.

In certain embodiments, the present invention relates to any of the aforementioned methods and any of the attendant limitations, wherein the first component is fabricated from silicon, polystyrene, quartz, glass, fused silica, SU-8, PDMS, polypropylene, epoxies, polymers, ceramics or metals.

In certain embodiments, the present invention relates to any of the aforementioned methods and any of the attendant limitations, wherein the second component is fabricated from silicon, polystyrene, quartz, glass, fused silica, SU-8, PDMS, polypropylene, epoxies, polymers, ceramics or metals.

In certain embodiments, the present invention relates to any of the aforementioned methods and any of the attendant limitations, wherein the first component is partially or completely coated with polystyrene.

In certain embodiments, the present invention relates to any of the aforementioned methods and any of the attendant limitations, wherein the second component is partially or completely coated with polystyrene.

In certain embodiments, the present invention relates to any of the aforementioned methods and any of the attendant limitations, wherein the first component is partially or completely coated with collagen.

In certain embodiments, the present invention relates to any of the aforementioned methods and any of the attendant limitations, wherein the second component is partially or completely coated with collagen.

In certain embodiments, the present invention relates to any of the aforementioned methods and any of the attendant limitations, wherein the first component is fabricated from an optically transparent material.

In certain embodiments, the present invention relates to any of the aforementioned methods and any of the attendant limitations, wherein the first component is fabricated from an optically translucent material.

In certain embodiments, the present invention relates to any of the aforementioned methods and any of the attendant limitations, wherein the second component is fabricated from an optically transparent material.

In certain embodiments, the present invention relates to any of the aforementioned methods and any of the attendant limitations, wherein the second component is fabricated from an optically translucent material.

In certain embodiments, the present invention relates to any of the aforementioned methods and any of the attendant limitations, wherein the at least one cell of the first type is different that the at least one cell of a second type.

In certain embodiments, the present invention relates to any of the aforementioned methods and any of the attendant limitations, wherein the at least one cell of a first type is a plurality of cells of a first type; the at least one cell of a second type is a plurality of cells of a second type; and the plurality of cells of the first type are different than the plurality of cells of the second type.

In certain embodiments, the present invention relates to any of the aforementioned methods and any of the attendant limitations, further comprising the step of altering the distance between the first component and the second component.

In certain embodiments, the present invention relates to any of the aforementioned methods and any of the attendant limitations, further comprising the step of replacing the first component or the second component with a third component; wherein the third component wherein the third component comprises at least one cell of a third type, different from the first type of cell and the second type of cell.

EXEMPLIFICATION

The invention now being generally described, it will be more readily understood by reference to the following examples, which are included merely for purposes of illustration of certain aspects and embodiments of the present invention, and are not intended to limit the invention.

Materials. Collagen-I was purified from rat tails as previously described. Dunn, J. C., Tompkins, R. G. & Yarmush, M. L. (1991) *Biotechnol Prog* 7, 237-45. Briefly, rat-tail tendons were denatured in acetic acid, salt-precipitated, dialyzed against HCl, and sterilized with chloroform. Since the silicon substrates are opaque, a reflecting non-inverted microscope is required to inspect cells during culture. In order to examine cultures without compromising sterility, a microscopy system was required with an optical working distance greater than the thickness of a covered culture plate. A 5× objective with 36 mm working distance and a 10× objective with a 38 mm working distance (Optical Product Development, Lexington, Mass.) mounted on a Meiji MA655/05 head (Microscope World, Encinitas, Calif.) was used.

Device Fabrication. Microfabrication facilities were utilized at the University of California, Berkeley (U.C. Berkeley Microfabrication Laboratory, Berkeley, Calif.) and the Massachusetts Institute of Technology (Microsystems Technology Laboratories, Cambridge, Mass.), using a similar process at both locations. Device parts were fabricated using commonly utilized MEMS fabrication methods. Good references include papers by Ayon and coworkers (Ayon, A. A., Braff, R., Lin, C. C., Sawin, H. H. & Schmidt, M. A. (1999) *Journal of the Electrochemical Society* 146, 339-349) and Knobloch and coworkers (Knobloch, A. J., Wasilik, M., Fernandez-Pello, C. & Pisano, A. P. (2003) in 2003 *ASME International Mechanical Engineering Congress* (American Society of Mechanical Engineers, New York, N.Y. 10016-5990, United States, Washington, D.C., United States), Vol. 5, pp. 115-123). Briefly, a double-sidepolished silicon wafer (4", 500-μm, University Wafer, South Boston, Mass.) was oxidized (1000° C., $O_2/H_2O$) to grow a 1-μm layer of silicon dioxide. A layer of thick photoresist (Megaposit SPR220, Rohm and Hass, Philadelphia, Pa.) was spin-coated, patterned using a chrome mask and contact alignment (Karl Suss MA6, SUSS MicroTec Inc., Waterbury Center, Vt.), and developed (LDD-26W, Shipley, Marlborough, Mass.). The patterned wafer, or device wafer, was then attached to a handle wafer using a photoresist bond. After etching through the oxide layer ($He/CHF_3/CF_4$ plasma), deep reactive ion etching (ICP-ASE, Surface Technology Systems, Newport, UK) was used to etch through the entire device wafer as previously described (Knobloch, A. J., Wasilik, M., Fernandez-Pello, C. & Pisano, A. P. (2003) in 2003 *ASME International Mechanical Engineering Congress* (American Society of Mechanical Engineers, New York, N.Y. 10016-5990, United States, Washington, D.C., United States), Vol. 5, pp. 115-123). The parts were then released in acetone and cleaned in Piranha solution (4:1 $H_2SO_4:H_2O_2$, 120° C., 10 min). Finally, the silicon surface was functionalized for cell culture by spin-coating with polystyrene (100 mg/ml in toluene, 2400 rpm, 1 min) followed by plasma treatment ($O_2$, 200 mT, 200 W, 1 min), resulting in a surface comparable to tissue culture plastic. Devices can be reused multiple times (>20). Between experiments, the parts are cleaned in toluene followed by Piranha solution, and polystyrene is reapplied.

Alternative Approach to Device Fabrication. As described above, the silicon device components can cut out of a silicon wafer using a plasma etching process. In the first mask design described above, each device component was cut completely free of the silicon wafer—at the end of the plasma etch, the finished components had no connection with the rest of the wafer. The components were still attached by an adhesive to an underlying substrate. However, if the adhesive failed, which was not uncommon, the components could detach during the etch process, resulting in damage to the components. In an alternative mask design, the components were not etched completely free but instead remained connected to the rest of the wafer by small tethers. After etching was complete, a dicing saw was used to cut the tethers and free the components. This method resulted in a much higher yield (80% vs. 20%) in manufacturing.

The devices do not need to be made from silicon. For example, polyurethane, polystyrene, epoxy, acrylic, glass, or pre-strained polystyrene that shrinks upon heating, may be used. Methods such as casting, molding, laser cutting, water-jet cutting, machining, drill-press, injection molding, knife cutting can aid in the preparation of the devices.

Cell Culture. Primary hepatocytes were isolated from 2- to 3-month-old adult female Lewis rats (Charles River Laboratories, Wilmington, Mass.) weighing 180-200 g, following a modified procedure of Seglen (Seglen, P. O. (1976) *Methods Cell Biol* 13, 29-83). Detailed procedures for hepatocyte isolation and purification have been previously described (Dunn, J. C., Tompkins, R. G. & Yarmush, M. L. (1991) *Biotechnol Prog* 7, 237-45). Hepatocyte culture medium consisted of Dulbecco's Modified Eagle Medium with high glucose, 10% (v/v) fetal bovine serum, 0.5 U/mL insulin, 7 ng/mL glucagon, 7.5 g/mL hydrocortisone, and 1% (v/v) penicillin-streptomycin. Swiss 3T3 fibroblasts were purchased from ATCC (Manassas, Va.). J2-3T3 fibroblasts were the gift of Howard Green (Harvard Medical School, Cambridge, Mass.; Rheinwald, J. G. & Green, H. (1975) *Cell* 6, 331-43). Fibroblast culture medium consisted of Dulbecco's Modified Eagle Medium with high glucose, 10% bovine calf serum, and 1% penicillinstreptomycin.

Device Actuation. Actuation was performed within a biosafety cabinet using stainless steel tweezers (2-mm round tips), sterilized in 70% ethanol before use. Substrates were pushed or picked up using the round hole at the rear of each part. It is possible for the parts to lock together misaligned vertically. Therefore, after configuring substrates in the intended state, plates were covered and examined under the reflecting microscope to verify that interlocked fingers were in-plane. Typically, roughly 5% of interlocked parts were misaligned. To fix alignment, parts were simply separated and locked back together.

Seeding Of Cells Onto Micromechanical Substrates. Polystyrene-coated silicon substrates were placed into individual wells on standard 12-well culture plates. Substrates intended to support hepatocytes were incubated in collagen solution (400 μg/ml in water) at 37° C. for at least 45 min. To provide a flat, uniform surface for seeding, substrates were each locked together with a complementary part, in the contact mode. These complementary parts were utilized only during cell seeding and were set aside afterwards. Substrates were sterilized by soaking in 70% ethanol for 1 hand then washed twice in distilled water. Primary hepatocytes were typically seeded onto the male parts (no arms), while fibroblasts (Swiss 3T3 or J2-3T3) were seeded onto the female parts (with arms) (FIG. 1A). Cells were seeded at 500,000 cells/ml, with 1 mL per well, in the appropriate culture medium and incubated for 60 min at 37° C. Plates were shaken every 20 min to resuspend unattached cells. After 60 min, unattached cells were aspirated, the substrate was washed with culture medium, and seeding was repeated with a fresh cell suspension. This process was repeated until the substrate surface was fully coated, usually requiring 2-4 seeding cycles for hepatocytes and 2 seeding cycles for fibroblasts. Within 6 hours of completing cell seeding, the complementary parts were removed from each substrate. Cell-coated substrates were then transferred to fresh wells and incubated overnight in the appropriate medium. The following day, a cell scraper (Fisher Scientific, Pittsburgh, Pa.) was utilized to remove hepatocytes from the rear half of the substrates, in order to leave only the cells attached directly on the comb fingers (plus a border of roughly 1 mm due to imprecise manual scraping) (FIG. 1A, inset). Hepatocyte- and fibroblast-coated substrates were then assembled into their initial configurations for a particular experiment.

Fluorescent Labels. Hepatocytes were labeled using calcein AM (Molecular Probes, Eugene, Oreg.) at 5 µg/ml in hepatoctye medium. Swiss 3T3 fibroblasts were labeled using CellTracker Orange CMTMR (Molecular Probes) at 0.5 µM in serum-free fibroblast medium. J2-3T3 fibroblasts were labeled using CellTracker Blue CMAC (Molecular Probes) at 2.5 µM in serum-free fibroblast medium. For high-magnification images, hepatocyte membranes were labeled using PHK67 (Sigma-Aldrich, St. Louis, Mo.) at 1:1000 in Diluent C (Sigma). Fibroblast membranes were labeled using Vybrant DiI (Molecular Probes) at 5 µl/ml in serum-free fibroblast medium. Cell nuclei were labeled using Hoechst 33258 (Molecular Probes) at 0.001% in hepatocyte medium.

Functional Assays. Albumin content was measured using enzyme linked immunosorbent assays (MP Biomedicals, Irvine, Calif.) with horseradish peroxidase detection and 3,3',5,5'-tetramethylbenzidine (Pierce Biotechnology, Rockford, Ill.) as a substrate (Dunn, J. C., Tompkins, R. G. & Yarmush, M. L. (1991) *Biotechnol Prog* 7, 237-45). All experiments were performed at least twice, with triplicate samples for each condition. One representative outcome is presented for each experiment, with similar trends observed in multiple trials. Fluorescence quantification was performed using MetaVue 6.2r0 software (Universal Imaging Corporation, Downingtown, Pa.).

INCORPORATION BY REFERENCE

All of the U.S. patents and U.S. published patent applications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A method for dynamically controlling a co-culture of cells, comprising the steps of:
   (a) culturing at least one cell of a first type on a first micromechanical substrate, thereby providing a first population of cells;
   (b) culturing at least one cell of a second type on a second micromechanical substrate, thereby providing a second population of cells;
   (c) placing the first micromechanical substrate in contact with the second micromechanical substrate for a first period of time, thereby providing direct cell-cell contact between the first population of cells and the second population of cells; and
   (d) placing the first micromechanical substrate at a distance from the second micromechanical substrate for a second period of time, thereby preventing direct cell-cell contact between the first population of cells and the second population of cells while providing exposure to soluble factors produced by the first or second population of cells, wherein the distance is in the range of about 1 µm to about 1,000 µm;
   thereby dynamically controlling the co-culture of cells.

2. The method of claim 1, wherein the at least one cell of a first type is a plurality of cells of a first type; the at least one cell of a second type is a plurality of cells of a second type; the cells of a first type are target cells comprising a receptor; the cells of a second type secrete a soluble signal; and the co-culturing results in exposing cells to cytokines.

3. The method of claim 2, further comprising the step of determining the effect of a soluble signal exposure on the cells of a first type.

4. The method of claim 2, wherein the cells of a first type are mammalian cells.

5. The method of claim 2, wherein the cells of a first type are human cells.

6. The method of claim 2, wherein the cells of a first type comprise receptors for a member of the VEGF family, VEGF-D, a member of the MIP family, MIP- 1γ, ceruloplasmin, nitric oxide, gases, or growth factors.

7. The method of claim 2, wherein the cells of a first type comprise DLK, Dlk-1, a cadherin, or T- cadherin.

8. The method of claim 2, wherein the cells of a second type are mammalian cells.

9. The method of claim 2, wherein the cells of a second type are human cells.

10. The method of claim 2, wherein the cells of a second type secrete hematopoietins, interferons, tumor necrosis factors, chemokines, or a combination thereof.

11. The method of claim 2, wherein the cells of a second type secrete a member of the VEGF family, VEGF-D, a member of the MIP family, MIP-1γ, ceruloplasmin, nitric oxide, gases, or growth factors.

12. The method of claim 1, wherein the at least one cell of a first type is a plurality of cells of a first type; the at least one cell of a second type is a plurality of cells of a second type; the cells of a first type are target cells comprising a cytokine receptor; the cells of a second type secrete a cytokine; and the co-culturing results in exposing cells to cytokines.

13. The method of claim 12, further comprising the step of determining the effect of a cytokine exposure on the cells of a first type.

14. The method of claim 12, wherein the cells of a first type are mammalian cells.

15. The method of claim 12, wherein the cells of a first type are human cells.

16. The method of claim 12, wherein the cells of a first type comprise cytokine receptors selected from the group consisting of hematopoietin family receptors, interferon family receptors, tumor necrosis factor family receptors, and chemokine family receptors.

17. The method of claim 12, wherein the cells of a first type comprise cytokine receptors selected from the group consisting of receptors for IL-1 α, IL-I β, IL-2, IL3, IL-4, IL-5, IL-6, IL-7, IL-8, IL-9, IL-12, IL-15, GM-CSF, IFN-α, IFN-β, IFN-γ, TNF-α, TNF-β, CD40, Fas, MIP-1 α, MIP-1 β, RANTES, CCR5, and CXCR4.

18. The method of claim 12, wherein the cells of a second type are mammalian cells.

19. The method of claim 12, wherein the cells of a second type are human cells.

20. The method of claim 12, wherein the cells of a second type secrete hematopoietins, interferons, tumor necrosis factors, chemokines, or a combination thereof.

21. The method of claim 12, wherein the cells of a second type secrete IL-1 α, IL-1 β, IL2, IL-3, IL-4, IL-S, IL-6, IL-7, IL-8, IL-9, IL-12, IL-15, GM-CSF, IFN- α, IFN-β, IFN- γ, TNF-α, TNF- β, CD40, Fas, MIP-1 α, MIP-1β, RANTES, CCR5, or CXCR4.

22. The method of claim 1, wherein the distance is in the range of about 10 µm to about 200 µm.

23. The method of claim 1, wherein the distance is in the range of about 50 μm to about 100 μm.

24. The method of claim 1, wherein the first substrate is fabricated from silicon, polystyrene, quartz, glass, fused silica, SU-8, PDMS, polypropylene, epoxies, polymers, ceramics or metals.

25. The method of claim 1, wherein the second substrate is fabricated from silicon, polystyrene, quartz, glass, fused silica, SU-8, PDMS, polypropylene, epoxies, polymers, ceramics or metals.

26. The method of claim 1, wherein the first substrate is partially or completely coated with polystyrene.

27. The method of claim 1, wherein the second substrate is partially or completely coated with polystyrene.

28. The method of claim 1, wherein the first substrate is partially or completely coated with collagen.

29. The method of claim 1, wherein the second substrate is partially or completely coated with collagen.

30. The method of claim 1, wherein the first substrate is fabricated from an optically transparent material.

31. The method of claim 1, wherein the first substrate is fabricated from an optically translucent material.

32. The method of claim 1, wherein the second substrate is fabricated from an optically transparent material.

33. The method of claim 1, wherein the second substrate is fabricated from an optically translucent material.

34. The method of claim 1, wherein the at least one cell of a first type is not the same as the at least one cell of the second type.

* * * * *